United States Patent
Piferi et al.

(10) Patent No.: US 8,099,150 B2
(45) Date of Patent: Jan. 17, 2012

(54) MRI-COMPATIBLE HEAD FIXATION FRAME WITH COOPERATING HEAD COIL APPARATUS

(75) Inventors: Peter Piferi, Orange, CA (US); Christopher Keidl, Hartland, WI (US); David Peterson, Archer, FL (US)

(73) Assignee: MRI Interventions, Inc., Memphis, TN (US)

( * ) Notice: Subject to any disclaimer, the term of this patent is extended or adjusted under 35 U.S.C. 154(b) by 646 days.

(21) Appl. No.: 12/237,091

(22) Filed: Sep. 24, 2008

(65) Prior Publication Data
US 2009/0088627 A1    Apr. 2, 2009

Related U.S. Application Data

(60) Provisional application No. 60/974,821, filed on Sep. 24, 2007.

(51) Int. Cl.
*A61B 5/055* (2006.01)
(52) U.S. Cl. ........ 600/422; 600/417; 600/415; 600/421; 324/318
(58) Field of Classification Search ............... None
See application file for complete search history.

(56) References Cited

U.S. PATENT DOCUMENTS

| | | | |
|---|---|---|---|
| 5,388,580 A * | 2/1995 | Sullivan et al. | 600/421 |
| 6,198,961 B1 | 3/2001 | Stern et al. | |
| 6,315,783 B1 | 11/2001 | Katz et al. | |
| 7,706,858 B1 * | 4/2010 | Green et al. | 600/415 |
| 2002/0049451 A1 | 4/2002 | Parmer et al. | |
| 2002/0052610 A1 | 5/2002 | Skakoon et al. | |
| 2004/0215279 A1 | 10/2004 | Houben et al. | |
| 2004/0228796 A1 | 11/2004 | Talpade | |
| 2005/0054910 A1 * | 3/2005 | Tremblay et al. | 600/411 |
| 2005/0075650 A1 | 4/2005 | Dinkler | |
| 2007/0191706 A1 | 8/2007 | Calderon et al. | |
| 2007/0270683 A1 * | 11/2007 | Meloy | 600/415 |

FOREIGN PATENT DOCUMENTS

| | | |
|---|---|---|
| DE | 100 15 670 | 10/2001 |
| DE | 10029736 A1 | 1/2002 |
| WO | WO 96/02204 | 2/1996 |
| WO | WO 98/52064 A | 11/1998 |
| WO | WO 03/102614 A | 12/2003 |

OTHER PUBLICATIONS

Notification of Transmittal of the International Search Report and the Written Opinion of the International Searching Authority, or the Declaration for corresponding PCT Application No. PCT/US2008/011043 mailed Jan. 26, 2009.

* cited by examiner

*Primary Examiner* — Long V. Le
*Assistant Examiner* — Farshad Negarestan
(74) *Attorney, Agent, or Firm* — Myers Bigel Sibley & Sajovec, P.A.

(57) ABSTRACT

A head support assembly includes a base configured to be removably secured to an MRI scanner gantry, a head support frame attached to the base, and a longitudinally extending head coil apparatus adjustably secured to the head support frame. The head support frame includes a pair of elongated arms that extend outwardly in adjacent, spaced-apart, substantially co-planar relationship to form an area for receiving the head of a patient. Each arm includes a respective free end, and a head engagement rod is adjustably associated with each respective arm free end. The head engagement rods are configured to engage a patients head within the head support frame. One or more additional head engagement rods may extend outwardly from the head support frame between the pair of arms.

11 Claims, 25 Drawing Sheets

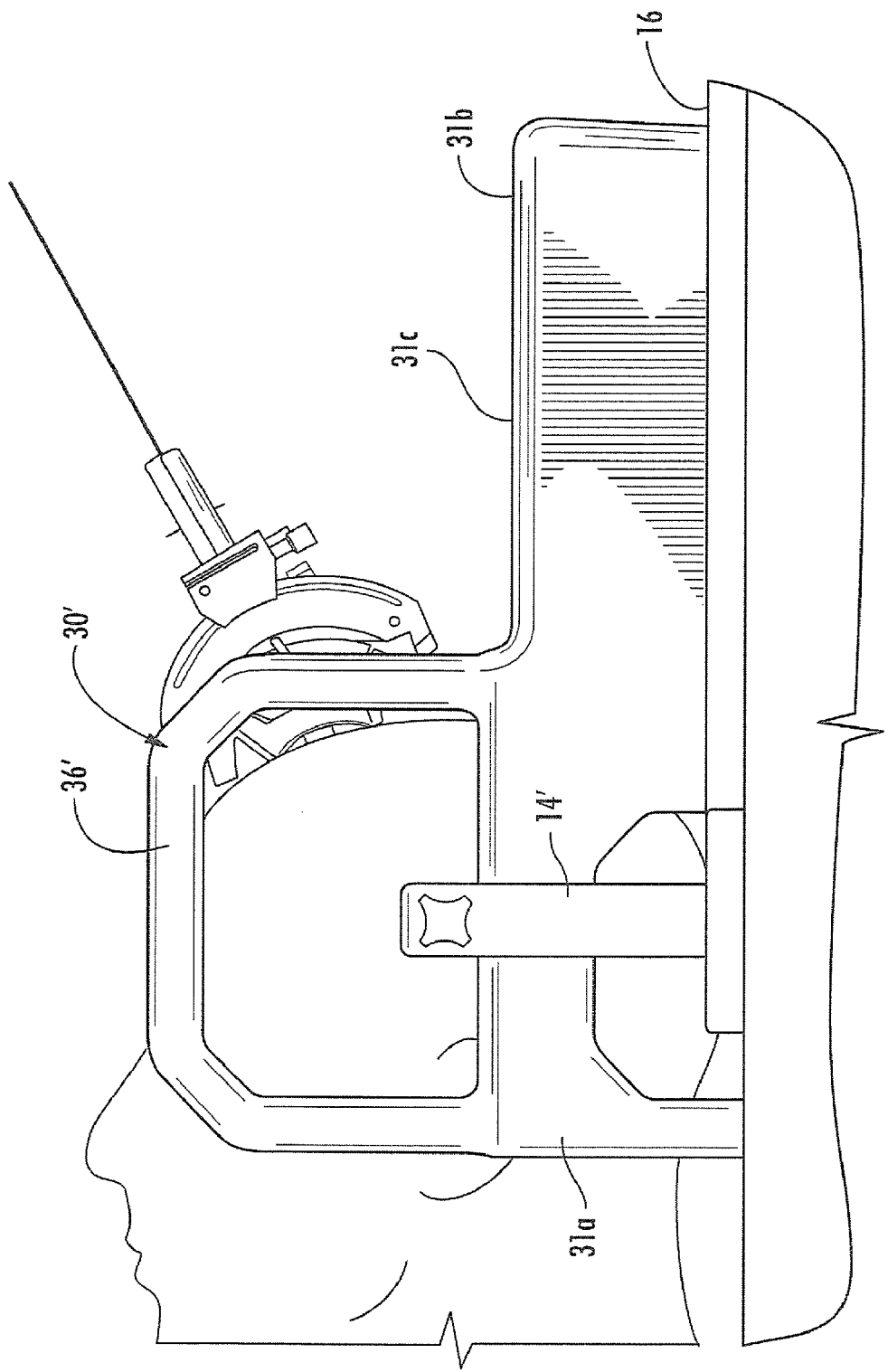

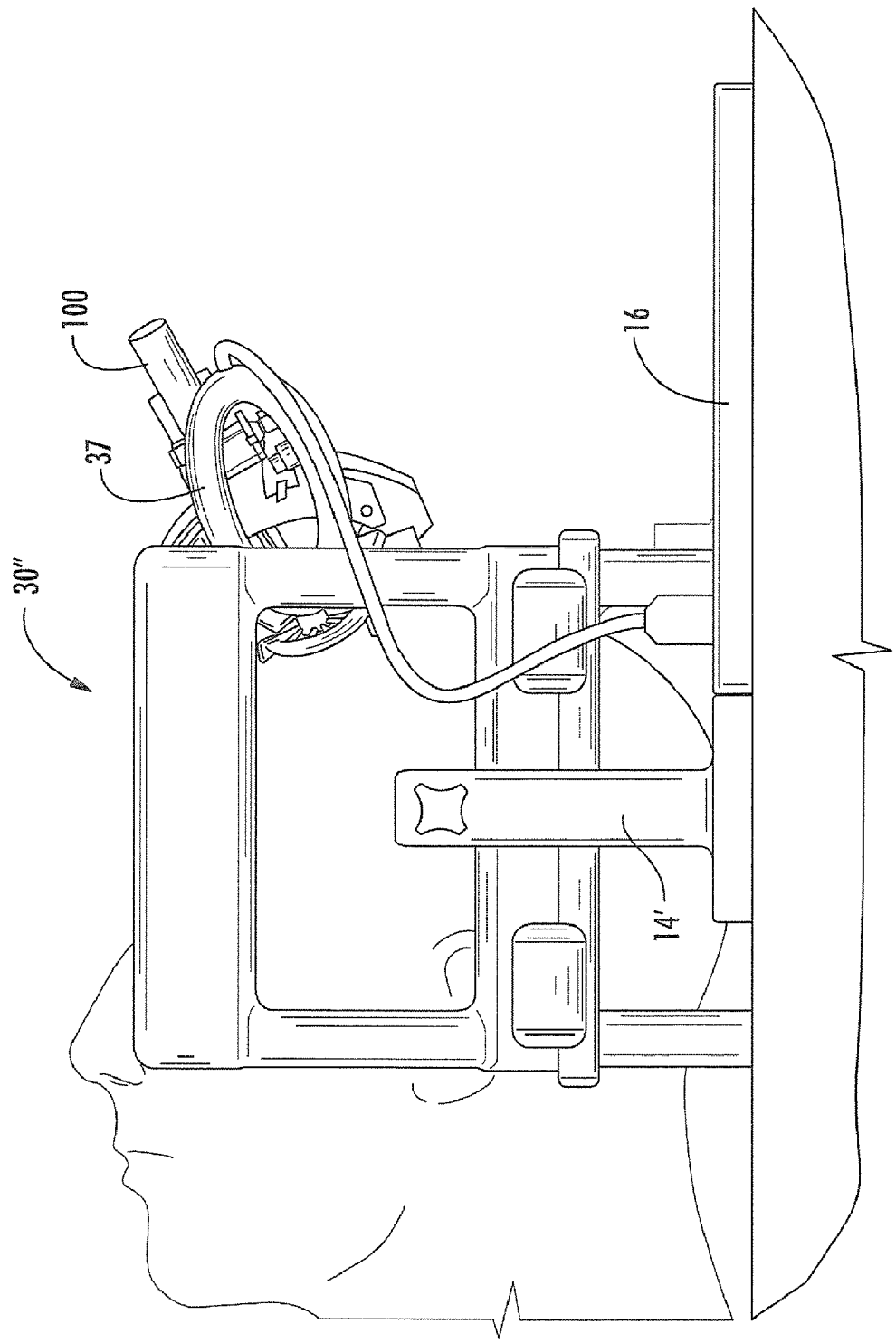

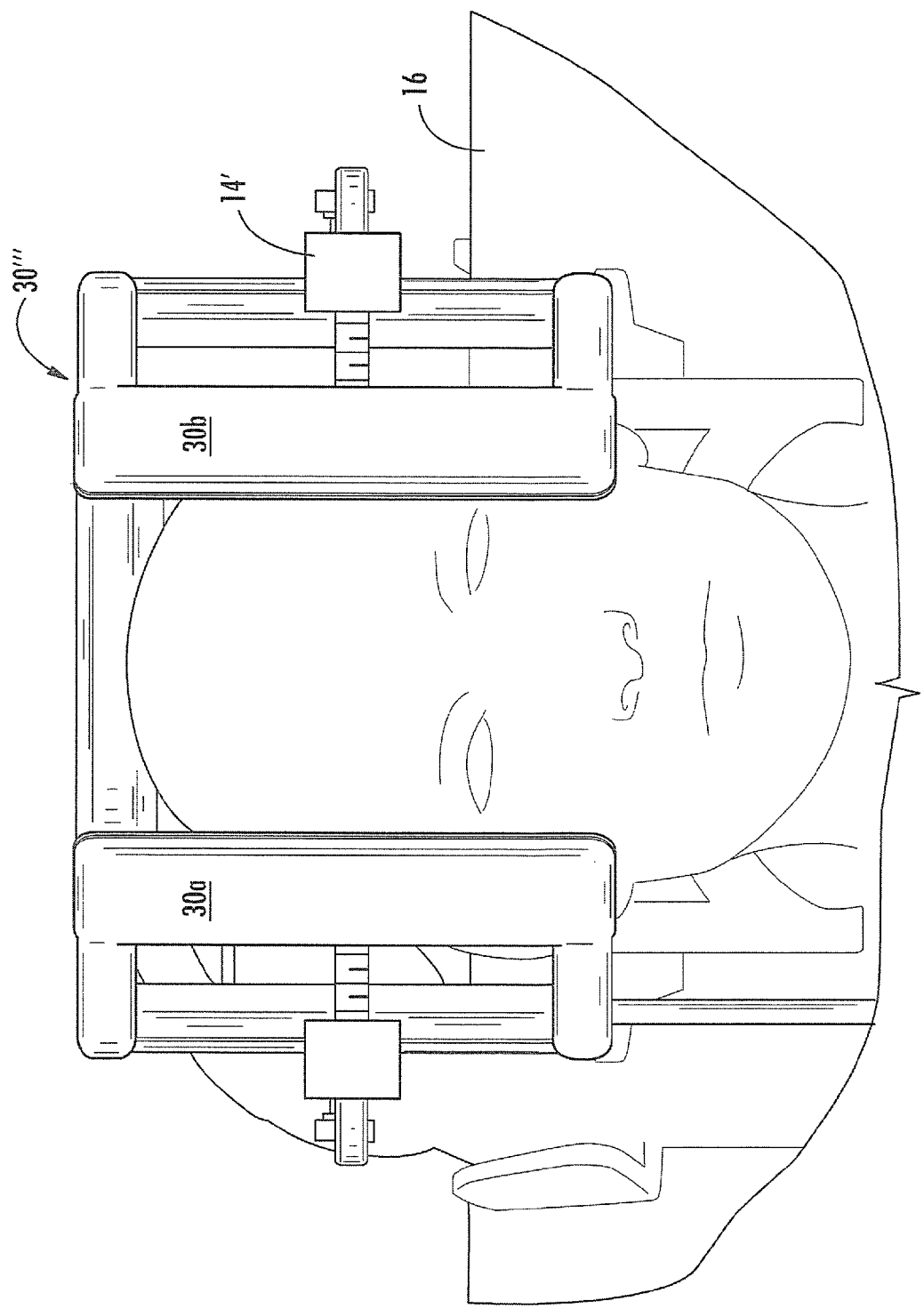

MRI-COMPATIBLE HEAD FIXATION FRAME WITH COOPERATING HEAD COIL APPARATUS

RELATED APPLICATIONS

This application claims the benefit of and priority to U.S. Provisional Patent Application No. 60/974,821, filed Sep. 24, 2007, and U.S. patent application Ser. No. 12/134,412, filed Jun. 6, 2008, the disclosures of which are incorporated herein by reference as if set forth in their entireties.

FIELD OF THE INVENTION

The present invention relates generally to medical systems and apparatus and, more particularly, to MRI-interventional systems and apparatus.

BACKGROUND

Deep Brain Stimulation (DBS) is becoming an acceptable therapeutic modality in neurosurgical treatment of patients suffering from chronic pain, Parkinson's disease or seizure, and other medical conditions. Other electro-stimulation therapies have also been carried out or proposed using internal stimulation of the sympathetic nerve chain and/or spinal cord, etc. One example of a prior art DBS system is the Activa® system from Medtronic, Inc. The Activa® system includes an implantable pulse generator stimulator that is positioned in the chest cavity of the patient and a lead with axially spaced apart electrodes that is implanted with the electrodes disposed in neural tissue. The lead is tunneled subsurface from the brain to the chest cavity connecting the electrodes with the pulse generator. These leads can have multiple exposed electrodes at the distal end that are connected to conductors which run along the length of the lead and connect to the pulse generator placed in the chest cavity.

It is believed that the clinical outcome of certain medical procedures, particularly those using DBS, may depend on the precise location of the electrodes that are in contact with the tissue of interest. For example, to treat Parkinson's tremor, presently the DBS probes are placed in neural tissue with the electrodes transmitting a signal to the thalamus region of the brain. DBS stimulation leads are conventionally implanted during a stereotactic surgery, based on pre-operative MRI and CT images. These procedures can be long in duration and may have reduced efficacy as it has been reported that, in about 30% of the patients implanted with these devices, the clinical efficacy of the device/procedure is less than optimum.

Real-time MRI-guided tools and procedures for DBS, as well as for other interventional medical procedures, are being developed. However, the quality of an MRI image depends on the strength of the received signal. As such radio frequency (RF) receiving coils typically are placed in close proximity to the area of a patient being imaged. These coils are often referred to as surface or head coils. One type of head coil used for imaging of the brain is a "bird cage" coil, as described in U.S. Pat. No. 6,396,271. Typically, a birdcage coil has a pair of circular end rings which are bridged by a plurality of equally-spaced straight segments or legs about the periphery of a cylindrical volume. A patient's head fits through one of the end rings and into the enclosed volume and a patient is typically unrestrained and able to move.

SUMMARY

In view of the above, improved head support assemblies for immobilizing the head of a patient during an MRI-guided procedure while providing access for interventional tools are provided. According to some embodiments of the present invention, a head support assembly includes a base configured to be removably secured to an MRI scanner gantry, a head support frame attached to the base, and a longitudinally extending head coil apparatus adjustably secured to the head support frame. The head support frame includes a pair of elongated arms that extend upwardly in adjacent, spaced-apart, relationship to form a space for receiving the head of a patient. Each arm includes a respective free end, and a head engagement rod is adjustably associated with each respective arm free end. The head engagement rods are configured to engage a patient's head within the head support frame and restrain the patient's head from movement.

One or more head engagement rods may extend from the head support frame between the pair of arms. These head engagement rods may be adjustably associated with the head support frame and are configured to engage a patient's head within the head support frame, and to prevent the head from pivoting. As such, the head of a patient is secured within, and aligned with respect to, a head coil apparatus by the head engagement rods.

In some embodiments, a surface of the head support frame between the pair of arms has a substantially concave configuration, and the elongated arms have an arcuate configuration such that the head support frame has a substantially U-shaped open-face configuration with open ends.

The head engagement rods associated with the elongated arms may extend along respective directions that are orthogonal to a longitudinal direction defined by the head support frame and head coil apparatus. Alternatively, the head engagement rods may extend along respective directions that are non-orthogonal to a longitudinal direction defined by the head support frame and head coil apparatus.

In some embodiments, the head engagement rods are threadingly engaged with the head support frame. For example, each elongated arm may include a threaded passageway formed therethrough, or a threaded boss associated therewith. A respective head engagement rod is threadingly engaged with each respective aperture or threaded boss. Similarly, threaded apertures or threaded bosses may be provided at other locations on the head support frame. A respective head engagement rod is threadingly engaged with each respective aperture or threaded boss in the head support frame.

The head coil apparatus includes a plurality of spaced-apart RF coils, and is configured to surround at least a portion of a patient's head supported by the head support frame. The head coil apparatus has a substantially open-face, U-shaped configuration with spaced-apart leg portions having free ends. The head coil apparatus can be adjustably secured to the head support frame between the head support frame arms such that leg portion free ends extend upwardly. Also, the head coil apparatus can be adjustable along a longitudinal direction relative to the head support frame. The open-face configuration of the head coil apparatus facilitates access to a patient by a physician/clinician, and/or interventional tools while providing sufficient signal-to-noise ratio (SNR) MRI signals.

In some embodiments, the head coil apparatus includes a pair of longitudinally spaced-apart, U-shaped supports, and a plurality of spaced apart members extending longitudinally between the supports. RF coils are associated with the spaced-apart members. In other embodiments, the head coil apparatus has a substantially unitary structure with a plurality of spaced-apart access windows formed therein. In some embodiments, the head coil apparatus has a flared or tapered end portion that further facilitates access to a patient by a physician/clinician.

In some embodiments, the head coil apparatus leg portions are movable (e.g., bendable, pivotable, etc.) to permit user adjustment of the spaced-apart relationship of the free ends. A user adjustable restraining device may also be attached to the respective leg portions to maintain a user-selected spaced-apart relationship of the free ends. In some embodiments, the restraining device is configured to contact a patient's head supported within the head support frame. In other embodiments, the restraining device does not contact a patient's head.

In some embodiments, the head coil apparatus shape and/or position is adjustable relative to the head support frame via spacers or shims positioned between the head coil apparatus and head support frame. These shims can allow a desired space to be maintained between the head support frame and the head coil apparatus.

In some embodiments, the head support frame includes a pair of head coil apparatus support rods that extend along respective directions that can be substantially parallel with the longitudinal direction of the head coil apparatus. The head coil apparatus is configured to be removably secured to these support rods. At least one of the head coil apparatus support rods is adjustably associated with the head support frame along the longitudinal direction such that longitudinal adjustment of the at least one coil support rod causes longitudinal adjustment of the head coil apparatus.

In some embodiments, a shield may be removably secured to the head support frame and is configured to shield non-MRI compatible objects used in conjunction with the head support assembly during an MRI-guided procedure. For example, cables and other conductive materials and devices utilized in a medical procedure can be shielded from RF excitation via the shield. The shield can be configured to protect against liquids, such as blood, and other materials that may cause damage to cables and electronic equipment, etc.

According to other embodiments of the present invention, a head support assembly for immobilizing the head of a patient during an MRI-guided procedure includes a base configured to be removably secured to an MRI scanner gantry, a head support frame attached to the base, and a longitudinally extending, open-face head coil apparatus secured to the base, wherein the head coil apparatus comprises a plurality of RF coils and is configured to surround at least a portion of a patient's head within the head support frame. The head coil apparatus includes opposite first and second end portions, with the first end portion positioned within the head support frame. The head coil apparatus includes a plurality of spaced-apart access windows formed therein. A plurality of head engagement rods are adjustably associated with the head support frame, and are configured to engage a patient's head within the head support frame. Each rod extends through a respective access window of the head coil apparatus.

The head coil apparatus includes a plurality of spaced-apart RF coils, and is configured to surround at least a portion of a patient's head supported by the head support frame. The head coil apparatus has a substantially open, U-shaped open-face configuration with spaced-apart leg portions having free ends. The head coil apparatus is adjustably secured to the head support frame between the head support frame arms such that leg portion free ends extend upwardly. Also, the head coil apparatus can be adjustable along a longitudinal direction relative to the head support frame for improved alignment to intrabody (deep brain, etc.) locations of various patient head sizes.

The head support frame includes a pair of substantially co-planar arcuate members extending outwardly from the base in adjacent, spaced-apart relationship to form a substantially U-shaped head support frame. Each arcuate member comprises a free end and a respective head engagement rod associated therewith. The head engagement rods associated with the elongated arm free ends may extend along respective directions that are orthogonal to a longitudinal direction defined by the head support frame and head coil apparatus. Alternatively, the head engagement rods can extend along respective directions that are non-orthogonal to a longitudinal direction defined by the head support frame and head coil apparatus.

In some embodiments, the head engagement rods are threadingly engaged with the head support frame. For example, each elongated arm may include a threaded aperture formed therein, or a threaded boss associated therewith, adjacent the free end. A respective head engagement rod is threadingly engaged with each respective aperture or threaded boss. Similarly, threaded apertures or threaded bosses may be provided at other locations on the head support frame. A respective head engagement rod is threadingly engaged with each respective aperture or threaded boss in the head support frame.

Head support assemblies according to embodiments of the present invention may be particularly suitable for placing neuro-modulation leads, such as Deep Brain Stimulation ("DBS") leads, implantable parasympathetic or sympathetic nerve chain leads and/or CNS stimulation leads, as well as other devices within the brain. Embodiments of the present invention may be suitable for a number of MRI-guided drug delivery procedures, MRI-guided ablation procedures, etc.

Head support assemblies according to embodiments of the present invention can be advantageous over conventional systems because they can be easily adjustable for various patient head sizes and shapes, and can support large forces exerted in any direction without movement, thereby providing stability to the head of a patient during various interventional procedures. In addition, head support assemblies according to embodiments of the present invention do not allow a patient's head to move in any direction, including pivotal movement. Moreover, head support assemblies according to embodiments of the present invention do not interfere with other components or a physician's access to the patient. Head support assemblies, according to embodiments of the present invention can be sterilized within an autoclave, and can be wiped down with disinfectant and cleaners. Head support assemblies, according to embodiments of the present invention can be installed and used many times without degradation, or may be single-use and disposable.

BRIEF DESCRIPTION OF THE DRAWINGS

FIGS. 8-9 illustrate that open-face head coil apparatus, according to embodiments of the present invention, can accommodate targeting cannulas and other interventional devices.

FIG. 10 illustrates an open-face head coil apparatus, according to some embodiments of the present invention.

DETAILED DESCRIPTION

Figure 1:
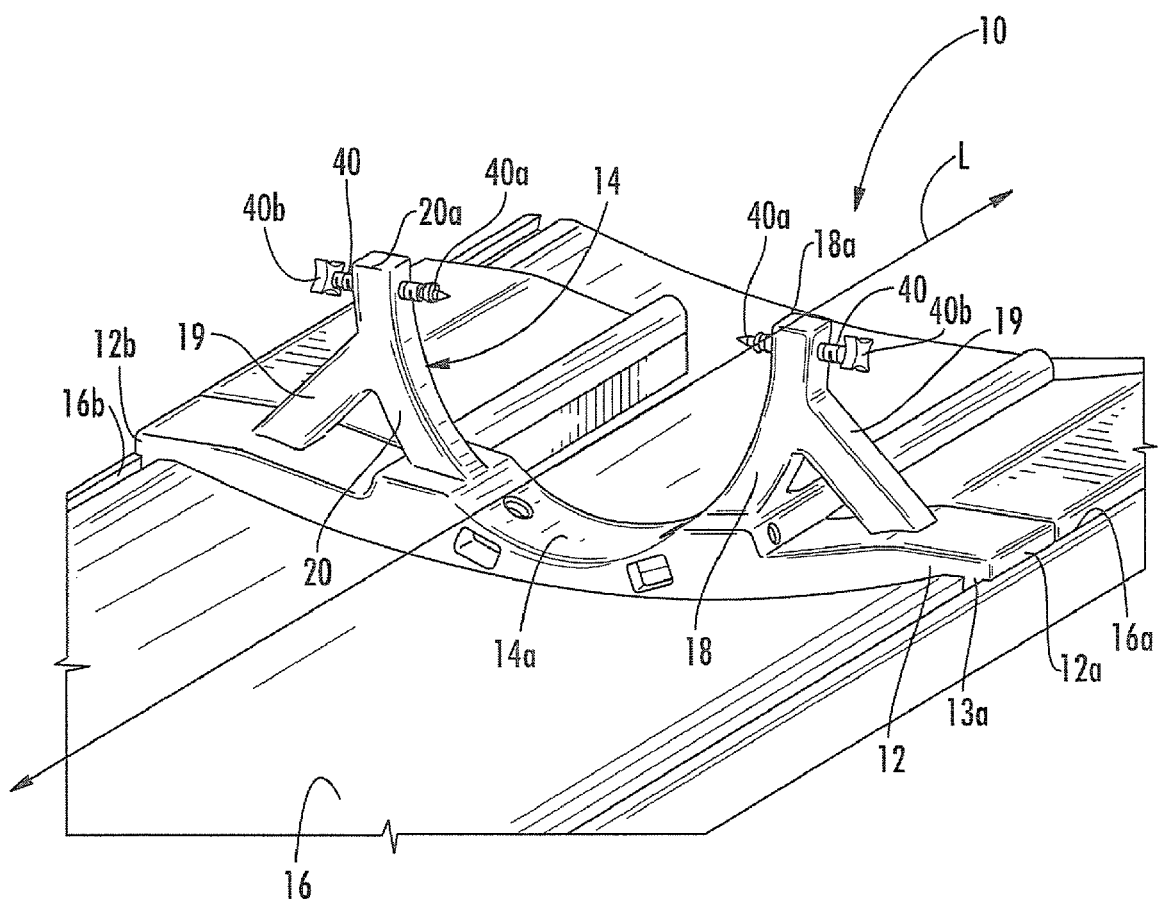
FIG. 1 is a perspective view of the head support frame of a head support assembly, according to some embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "MRI compatible" means that a device is safe for use in an MRI environment and/or can operate as intended in an MRI environment, and, as such, if residing within the high-field strength region of the magnetic field, is typically made of a non-ferromagnetic MRI compatible material(s) suitable to reside and/or operate in a high magnetic field environment.

The term "gantry" refers to a patient support of an MRI scanner and may include the patient table or other structure.

The term "rod" refers to an elongate member with rigidity, such as a bolt, pin, screw, etc. For example, a head engagement rod is an elongate member with sufficient structural rigidity to secure the head of a patient.

Head support assemblies according to embodiments of the present invention facilitate guiding and/or placing diagnostic or interventional devices and/or therapies to any desired internal region of the brain. For example, head support assemblies according to embodiments of the present invention facilitate the placement of implantable DBS leads for brain stimulation, typically deep brain stimulation, and facilitate delivering tools or therapies that stimulate a desired region of the sympathetic nerve chain. Embodiments of the present invention can be used with any MRI scanner system, including open and closed bore designs and any field strength, typically 1.0 T-10 T.

Embodiments of the present invention have other uses inside or outside the brain include stem cell placement, gene therapy or drug delivery for treating physiological conditions. Some embodiments can be used to treat tumors. Some embodiments can be used for diagnosing or delivering any desired therapy such as, for example, RF stimulation or ablation, laser stimulation or ablation, cryogenic stimulation or ablation, etc.

Embodiments of the present invention will now be described in detail below with reference to the figures. Referring initially to FIG. 1, a head support assembly 10 is illustrated without a head coil apparatus (FIG. 2) attached thereto. The illustrated head support assembly 10 includes a base 12 and a head support frame 14. The base 12 and head support frame 14 may be an integral unit, or may be separate components. In the illustrated embodiment, the head support frame 14 and base 12 are an integral unit. The base 12 is configured to be removably secured to the gantry 16 associated with an MRI scanner. In the illustrated embodiment, the base 12 includes opposite first and second end portions 12a, 12b. A downwardly extending portion 13a, 13b of each end portion 12a, 12b is configured to engage a respective groove 16a, 16b formed within and extending along the gantry 16 in substantially parallel, spaced-apart relationship, as illustrated. The cross sectional shape of each respective downwardly extending portion 13a, 13b is configured to matingly engage a respective groove 16a, 16b. For example, the downwardly extending portions 13a, 13b may have a trapezoidal or dovetail configuration (FIG. 3). Each groove 16a, 16b has a corresponding trapezoidal or dovetail shape.

To install the illustrated base 12, downwardly extending portions 13a, 13b engage the respective grooves 16a, 16b at a free end of the gantry 16 and the base 12 and the frame 14 are moved along the gantry 16 to a selected position. One or more set screws or other locking mechanisms (not shown) may be utilized to maintain the base 12 at a selected location on the gantry 16.

Embodiments of the present invention, however, are not limited to the illustrated base 12 or to the illustrated engagement of base 12 and gantry 16. Furthermore, it is anticipated that a base for a head support assembly of the present invention can be customized to fit and be secured to any type of gantry. That is, the base may be a universal base usable with several different MRI scanners from different manufacturers, or may be MRI scanner type specific.

The illustrated head support frame 14 includes a pair of elongated arms 18, 20 that extend outwardly from the base 12 in adjacent, spaced-apart relationship to form a space for receiving the head of a patient. The illustrated arms 18, 20 lie in substantially the same plane (i.e., are substantially coplanar) and have an arcuate configuration. The surface 14a of the head support frame 14 between the pair of arms 18, 20 has a concave configuration. As such, the concave surface 14a and arcuate arms 18, 20 give the head support frame 14 a substantially U-shaped configuration. In the illustrated embodiment, a bracing member 19 is attached to each respective arcuate arm 18, 20 to provide rigidity and stability. However, head support frames according to embodiments of the present invention do not require bracing members. Moreover, head support frames according to embodiments of the present invention may have various structural configurations, without limitation.

The illustrated head support assembly 10 includes a longitudinally extending head coil apparatus 30 (FIG. 2) secured to the head support frame 14. The head coil apparatus 30 has an open-ace, substantially U-shaped configuration with spaced-apart leg portions 30a, 30b having free ends. The head coil apparatus 30 is secured to the head support frame 14 between the head support frame arms 18, 20 such that the free ends of the leg portions 30a, 30b extend upwardly, as illustrated. Also, the head coil apparatus 30 can be adjustable along a longitudinal direction L (FIG. 1) relative to the head support frame 14, as will be described below.

The illustrated open-face head coil apparatus 30 includes a pair of longitudinally spaced-apart, U-shaped supports 32, 34 and a plurality of spaced apart connecting members 36 that extend longitudinally between the supports 32, 34. RF coils are contained within at least some of the connecting members 36, along with the circuitry for controlling RF excitation of the RF coils. An exemplary supplier of RF coils that may be utilized is Midwest RF, LLC., Hartland, Wis. The head coil apparatus 30 is configured to surround at least a portion of a patient's head supported by the head support frame 14. As such, RF coils can be positioned as desired relative to a patient's head. Embodiments of the present invention are not limited to the configuration of the illustrated open-face head coil apparatus 30 of FIG. 2. Head coil apparatus 30 may have various shapes and configurations, but includes an open-face configuration.

Figure 2:
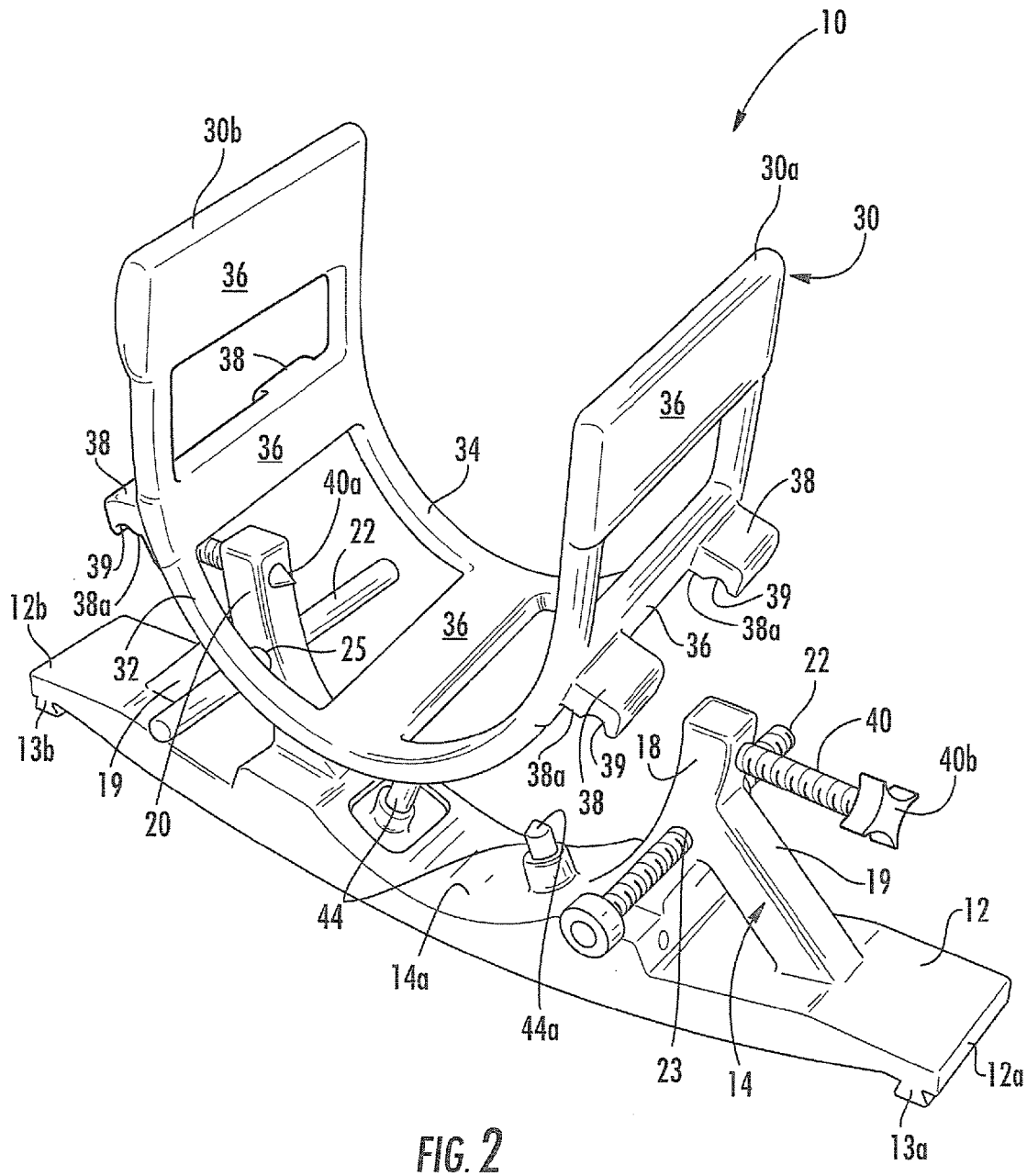
FIG. 2 illustrates the attachment of an open-face head coil apparatus that can cooperate with a head support frame, such as that shown in FIG. 1, according to some embodiments of the present invention.
Figure 3:
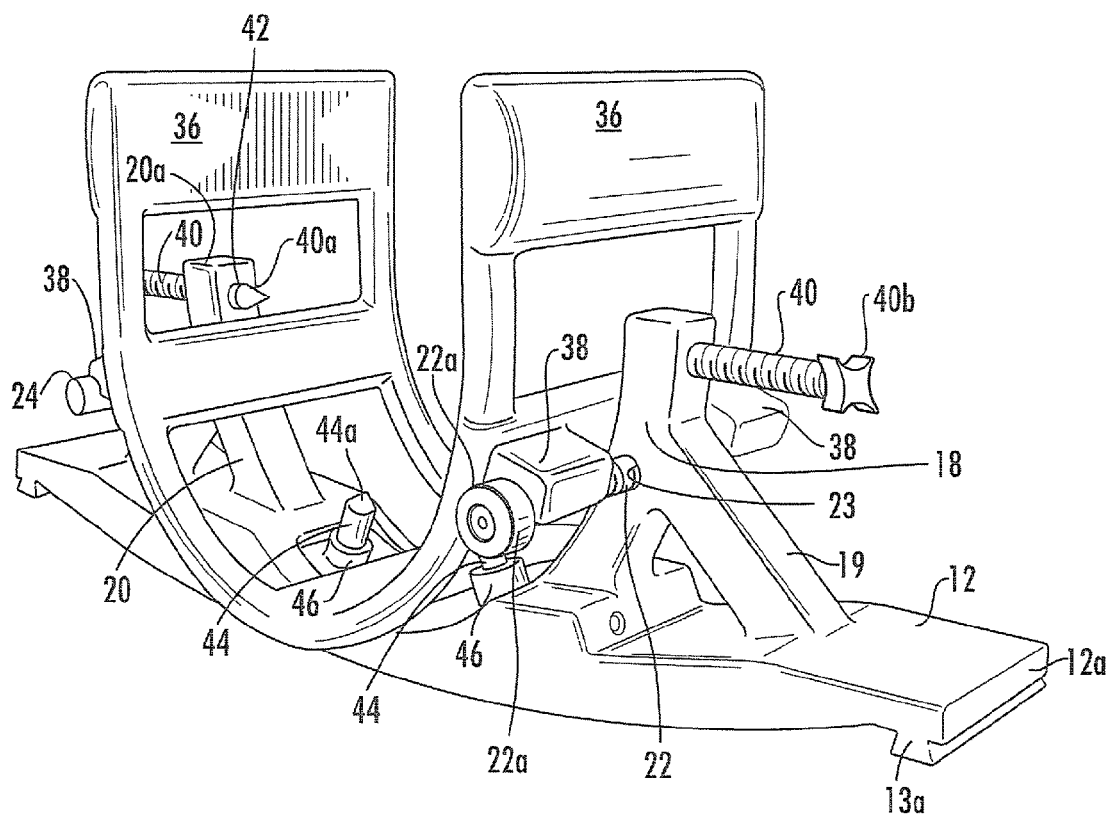
FIG. 3 is a perspective view of the open-face head coil apparatus of FIG. 2 removably and adjustably secured to the head support frame of FIG. 1, according to some embodiments of the present invention.

In some embodiments, the head coil apparatus 30 can include two pair of spaced apart shoulders 38 that extend outwardly from respective, opposing connecting members 36, as illustrated in FIGS. 2-3. The shoulders 38 are configured to support the head coil apparatus 30 on the frame 14 and to allow the head coil apparatus 30 to be adjustable along a longitudinal direction L (FIG. 1) relative to the head support frame 14. Each shoulder 38 includes a lower surface 38a with a longitudinally extending groove 39 formed therein that is configured to rest upon a longitudinally extending support rod associated with the head support frame 14. At least one of the support rods may be threaded so as to threadingly engage a respective threaded passageway formed within the head support frame 14.

In the illustrated embodiment, a threaded passageway 23 is formed through arcuate arm 18 and extends along a direction that is substantially parallel with the longitudinal direction L (although it need not be). Threaded head coil apparatus support rod 22 extends outwardly from both ends of the passageway 23 such that a pair of shoulders 38 on one side of the head coil apparatus 30 rests on the support rod 22. A passageway 25 is formed through arcuate arm 20 and extends along a direction that is substantially parallel with the longitudinal direction L (although it need not be). A head coil apparatus support rod 24 extends outwardly from both ends of the passageway 25 such that the other pair of shoulders 38 on the opposite side of the head coil apparatus 30 rests on the support rod 24.

Threaded support rod 22 includes an enlarged head portion 22a (FIG. 3) at one end thereof that facilitates rotation of the support rod 22 by a clinician. The enlarged head portion 22a may have a knurled circumference to facilitate gripping and rotation by a user, as would be understood by those skilled in the art. The head coil apparatus 30 is supported on threaded support rod 22 such that shoulder 38 abuts the head portion 22a. As such, clockwise rotation of the support rod 22 causes the head coil apparatus 30 to be moved one way along the longitudinal direction L. Counterclockwise rotation of the threaded support rod 22 will create a space between shoulder 38 and the enlarged head portion 22a, allowing the head coil apparatus to be moved by a clinician in the opposite way along the longitudinal direction L.

Embodiments of the present invention are not limited to the illustrated shoulders 38 and support rods 22, 24. Other ways of adjustably supporting the head coil apparatus 30 on the head support frame 14 may be utilized, without limitation.

Each arm 18, 20 of the head support frame 14 includes a respective free end 18a, 20a (FIG. 1). A head engagement rod 40 is adjustably associated near each respective arm free end 18a, 20a. The head engagement rods 40 are configured to engage a patient's head within the head support frame 14.

In the illustrated embodiment of FIG. 3, a threaded passageway 42 extends through each arcuate arm 18, 20 adjacent each respective free end 18a, 20a, as illustrated. A head engagement rod 40 is threaded and is configured to threadingly engage a respective threaded passageway 42. In the illustrated embodiment, each head engagement rod 40 includes opposite first and second end portions 40a, 40b. The first end portion 40a of each head engagement rod has a conical shape that is configured to engage the skull of a patient's head and make sufficient contact with the skull to maintain the patient's head in a desired orientation. The second end portion 40b of each head engagement rod 40 has an enlarged configuration that facilitates rotation of the head engagement rod 40 by a clinician. The enlarged second end portion 40b may have a knurled circumference to facilitate gripping and rotation by a clinician, as would be understood by those skilled in the art. Head engagement rods may be formed from various materials (e.g., titanium, etc.) and may be disposable. Alternatively, the first end portion 40a of each head engagement rod 40 may be removable (and disposable) from the remainder of the head engagement rod 40. The first end portion 40a of each head engagement rod 40 may be formed from various materials (e.g., titanium, etc.).

The threaded passageway 42 formed in each of the arcuate arms 18, 20 may extend along respective directions that are orthogonal to the longitudinal direction L (FIG. 1). Alternatively, the threaded passageway 42 formed in each of the arcuate arms 18, 20 may extend along a direction that is non-orthogonal to the longitudinal direction L. As such, head engagement rods 40 associated with the elongated arm free ends 18a, 20a may extend along respective directions that are orthogonal to the longitudinal direction L, or may extend along respective directions that are non-orthogonal to the longitudinal direction L. For example, in some embodiments, head engagement rods 40 may be angled downwardly, upwardly, forwardly, or rearwardly relative to the head support frame 14.

In the illustrated embodiment, a pair of additional head engagement rods 44 extend outwardly from the head support frame surface 14a between the pair of arms 18, 20. These additional head engagement rods 44 are adjustably associated with the head support frame 14 and are configured to engage and support a patient's head within the head support frame. The illustrated head engagement rods 44 have a conically-shaped end portion 44a that is configured to engage the skull of a patient's head and make sufficient contact with the skull to maintain the patient's head in a desired orientation. One or more of the head engagement rods 40, 44 may be particularly effective in preventing a patient's head from pivoting during fixation within the head support frame 14. As such, the head of a patient is secured within the head support frame 14 by the head engagement rods 40 associated with the head support frame arms 18, 20 and by head engagement rods 44 associated with the head support frame 14 between the arms 18, 20.

In some embodiments, the head engagement rods 44 are threadingly engaged with the head support frame 14. For example, in the illustrated embodiment, a pair of threaded bosses 46 extend from the portion of the head support frame 14 between the arcuate arms 18, 20. A respective head engagement rod 44 is threadingly engaged with each respective threaded boss 46.

The threaded bosses 46 may each have an axial direction that is orthogonal to the longitudinal direction L. Alternatively, the threaded bosses 46 may each have an axial direction that is non-orthogonal to the longitudinal direction L. As such, head engagement rods 44 associated may extend along respective directions that are orthogonal to the longitudinal direction L, or may extend along respective directions that are non-orthogonal to the longitudinal direction L. For example, in some embodiments, head engagement rods 44 may be angled forwardly or rearwardly relative to the head support frame 14.

Figure 24:
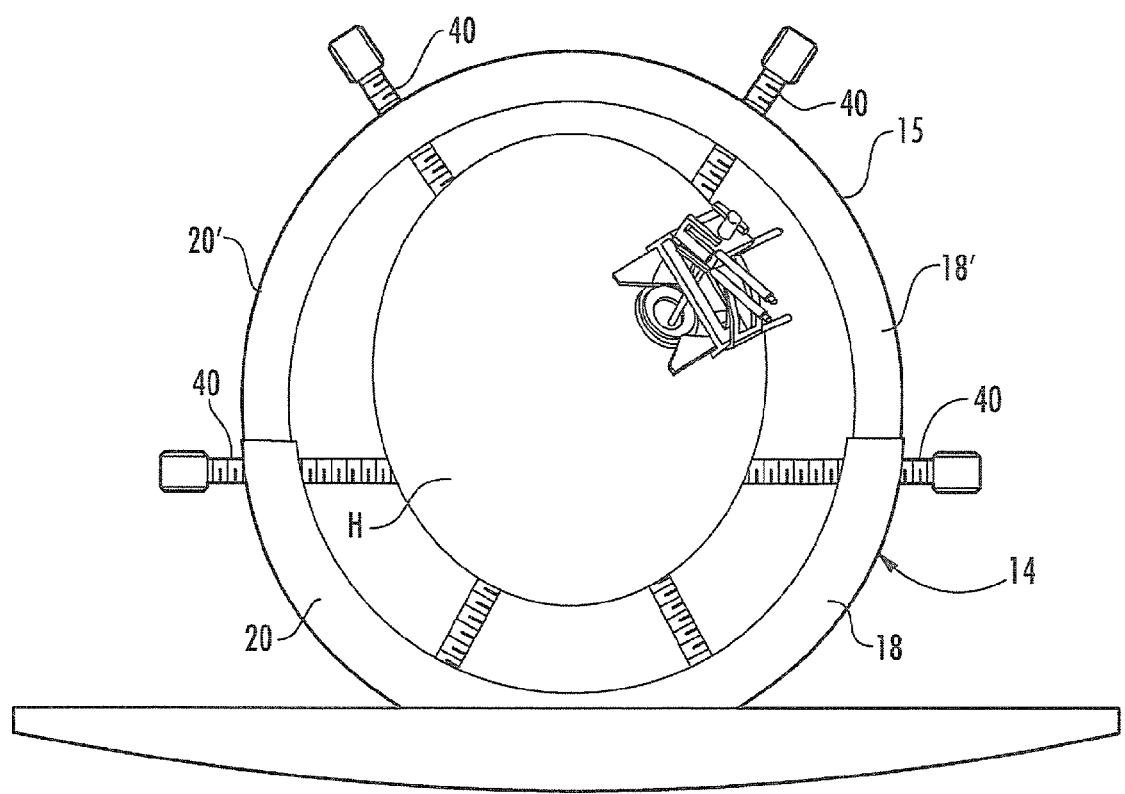
FIG. 24 is an end view of a head support frame of a head support assembly, according to other embodiments of the present invention.

Referring to FIG. 24, in some embodiments, a head support frame 14 can include a top portion 15 secured to arms 18, 20. The illustrated top portion 15 includes corresponding arms 18', 20' having an arcuate configuration that overlie the forehead of a patient. Thus, the illustrated head support frame of FIG. 24 completely surrounds the head H of a patient. A pair head engagement rods 40 are adjustably associated with the top portion 15 and are configured to engage a patient's head, as illustrated.

Figure 4:
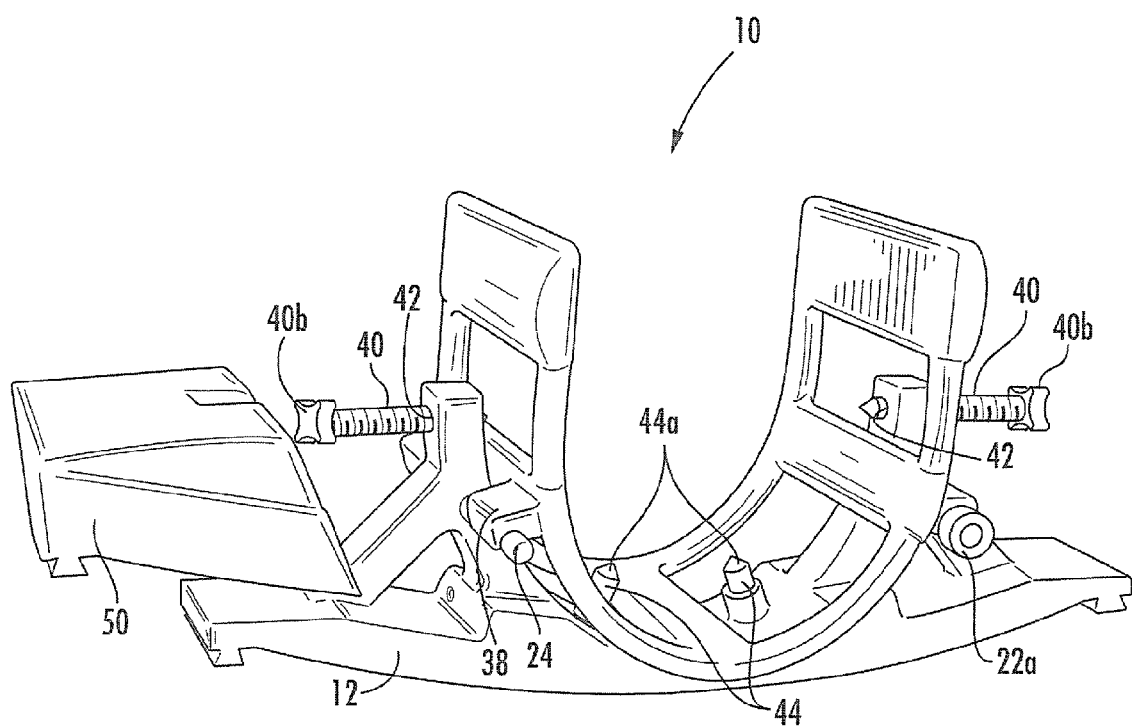
FIG. 4 illustrates a shield being removably secured to the head support frame of FIG. 1.
Figure 5:
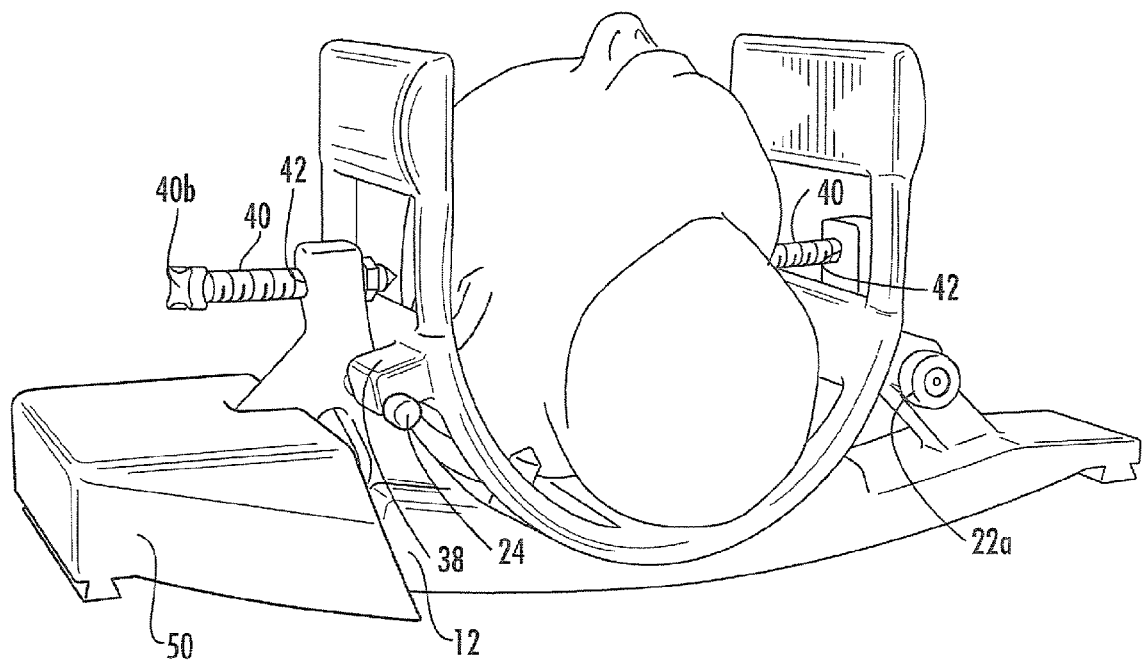
FIG. 5 illustrates the head of a patient being secured to the head support assembly of FIG. 3.
Figure 6:
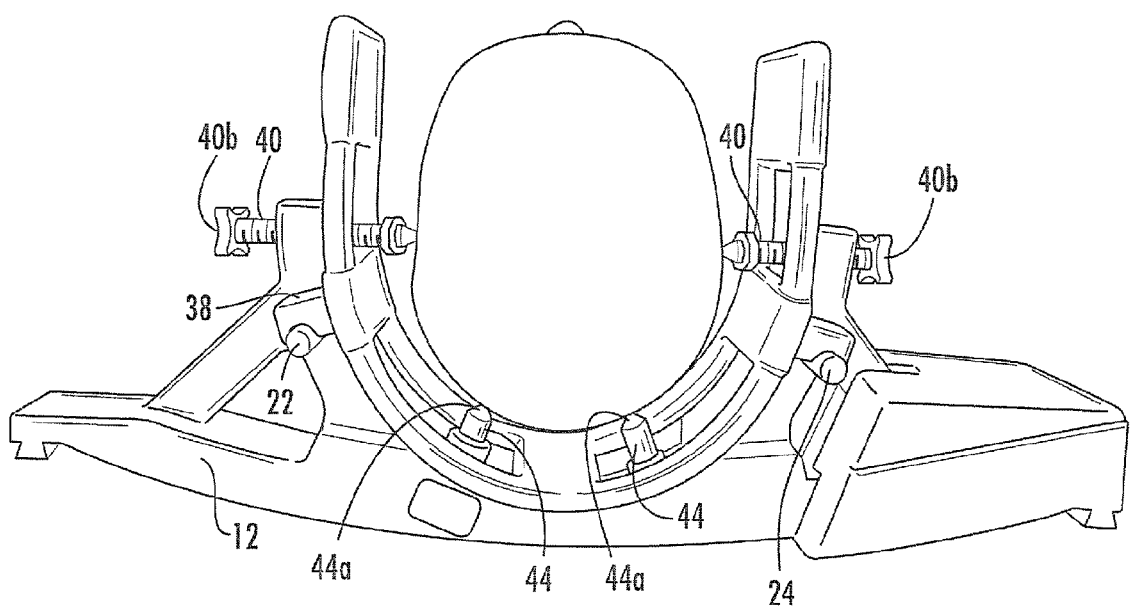
FIG. 6 is an end view of the head support assembly of FIG. 5 with the patient's head secured thereto.

Referring now to FIG. 4, the head support assembly 10 may also include a cover or shield 50 that is configured to cover electrical components, cables, and the like. In some embodiments, the shield 50 is configured to shield non-MRI compatible objects used in conjunction with the head support assembly 10 during an MRI-guided procedure. For example, cables and other conductive materials and devices utilized in a medical procedure can be shielded from RF excitation via the shield 50. The shield may be removably secured to the head support frame to facilitate access to cables and other devices used for various MRI guided procedures. In some embodiments, the shield 50 may be configured to protect against foreign material, including liquids, etc.

All of the components of the head support assembly 10 described above (i.e., the base 12, the head support frame 14, the head engagement rods 40, 44, the open-face head coil apparatus 30, and the shield 50) are formed from or include MRI-compatible material. Exemplary MRI-compatible materials include, but are not limited to, various polymeric materials (e.g., plastics), carbon fiber materials, glass-filled epoxies, and metals such as nickel-titanium alloys (e.g., Nitinol). As known to those skilled in the art of MRI, Nitinol is non-ferromagnetic with a lower magnetic susceptibility than conventional stainless steel.

Figure 7B:
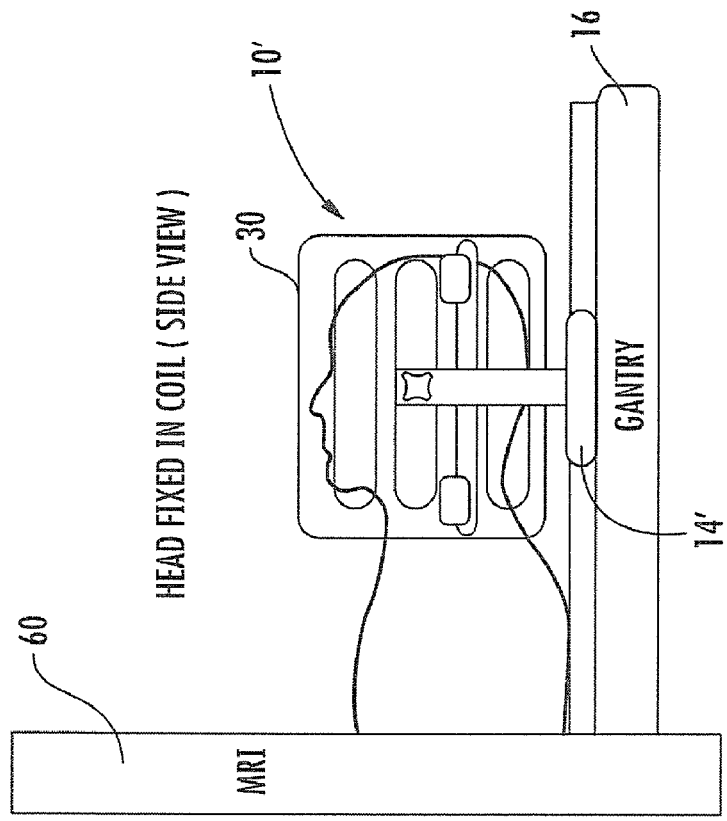
FIGS. 7A-7B are schematic illustrations of a patient on a gantry associated with the bore of an MRI scanner and wherein the head of the patient is secured to a head support assembly, according to some embodiments of the present invention.
Figure 7A:
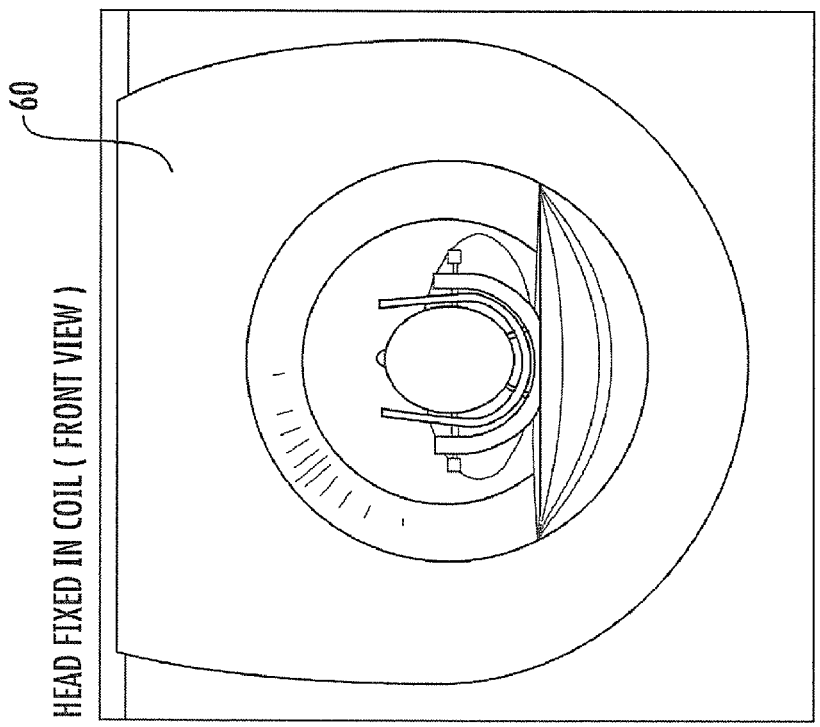

FIGS. 7A-7B are schematic illustrations of a patient on a gantry associated with the bore of an MRI scanner and wherein the head of the patient is secured to a head support assembly 10, according to some embodiments of the present invention. The illustrated head support assembly 10 includes a neurosurgical head support frame 14' secured to the gantry 16 of an MRI scanner 60. An open-face head coil apparatus 30 is adjustably secured to the head support frame 14' and is positioned around the head of a patient secured to the head support frame 14'. The head coil apparatus 30 has an open-face U-shaped configuration as described above with respect to FIGS. 2-6.

FIGS. 8-10 illustrate open-face head coil apparatus according to various embodiments of the present invention. In FIG. 8, an open-face head coil apparatus 30' includes opposite first and second end portions 31a, 31b. The head coil apparatus first end portion 31a is positioned within the head support frame 14'. The head coil apparatus second end portion 31b is secured to the gantry 16 of an MRI scanner. In other embodiments, head coil apparatus second end portion 31b can be secured to a movable base configured to allow adjustment of the position of the head coil apparatus 30. The illustrated head coil apparatus 30' includes spaced-apart, upwardly extending members 36' with open side windows and having an inverted, substantially U shape. RF coils, and associated circuitry for the RF coils are contained within the upwardly extending members 36' and/or second end portion 31b. In some embodiments, the illustrated head coil apparatus 30' includes an intermediate portion 31c between the first and second end portions 31a, 31b. Intermediate portion 31c may contain additional RF coils and associated circuitry. RF coils located in intermediate portion 31c can be positioned proximate to a targeting frame and/or other interventional device. In some embodiments, electronic components, cables, and circuitry for the head coil apparatus 30' can be stored within intermediate portion 31c.

In FIG. 9, an open-face head coil apparatus 30", similar to the head coil apparatus 30 of FIGS. 2-6, is positioned within a head support frame 14' and secured to the gantry 16 of an MRI scanner. A secondary RF coil 37 is provided and is positioned adjacent to a targeting frame 100 that is secured to the head of a patient. The secondary coil 37 can obtain local MRI signals and facilitates identifying the location of the targeting frame 100 during an MRI-guided procedure.

In FIG. 10, an open-face head coil apparatus 30''', similar to the head coil apparatus 30 of FIGS. 2-6, is positioned within a head support frame 14' and secured to the gantry 16 of an MRI scanner. The leg portions 30a, 30b of the head coil apparatus 30''' have an arcuate configuration such that each partially overlies the head of a patient.

Figure 11:
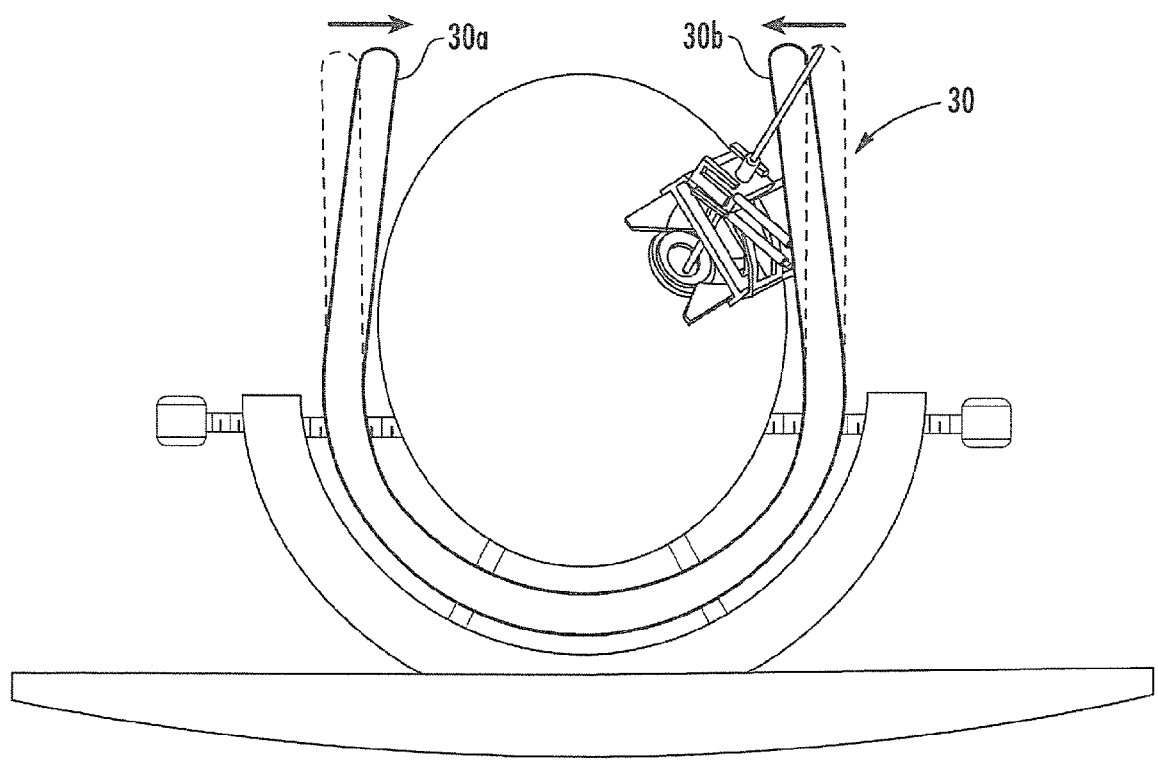
FIGS. 11-12 are schematic illustrations of a head support assembly wherein the legs of the open-face head coil apparatus are movable towards the head of a patient.
Figure 12:
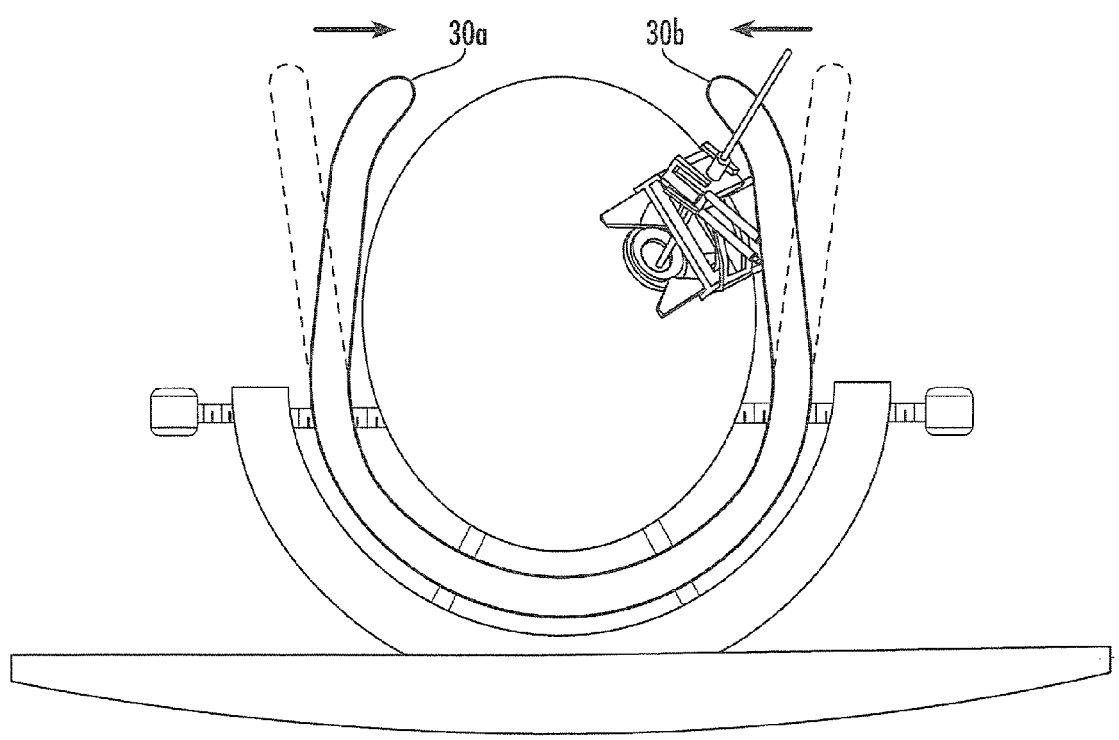

In some embodiments of the present invention, the leg portions of an open-face head coil apparatus are movable (e.g., bendable, deformable, pivotable, etc.) to permit user adjustment of the spaced-apart relationship of the leg portions 30a, 30b. For example, the leg portions 30a, 30b of head coil apparatus 30 may be configured to pivot relative to each other, as illustrated in FIG. 11. The leg portions 30a, 30b of head coil apparatus 30 may be configured to bend relative to each other, as illustrated in FIG. 12.

Figure 13:
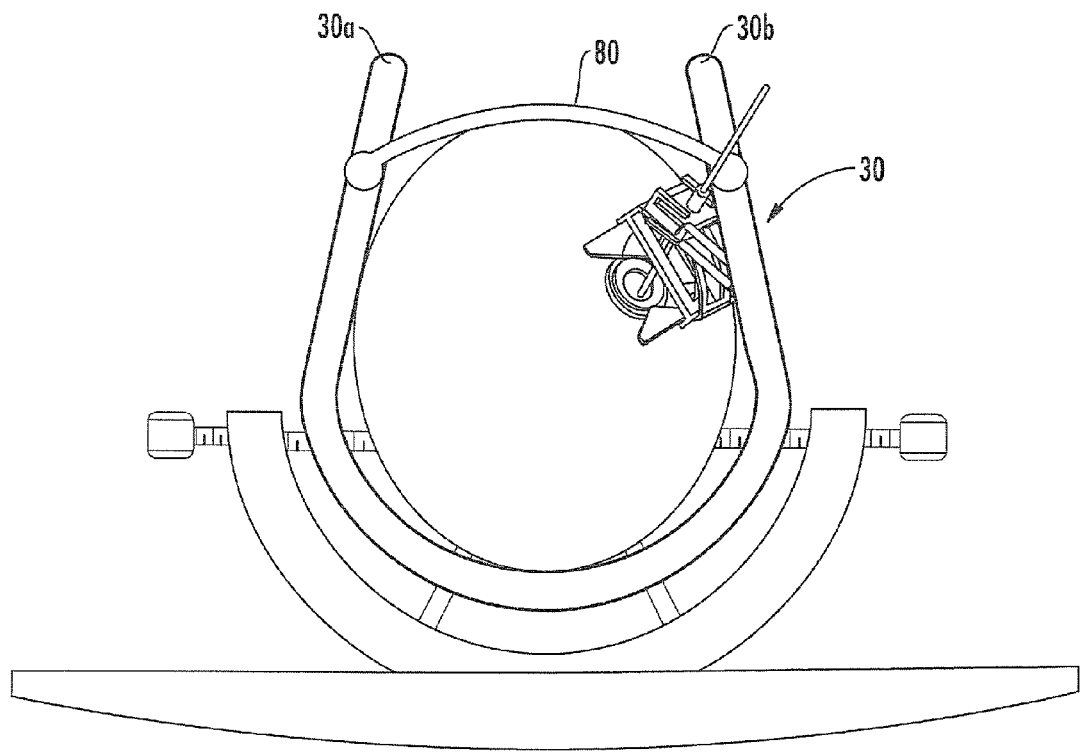
FIGS. 13-17 illustrate various embodiments of a restraint device for altering and/or maintaining the upper end portions of the legs of an open-face head coil apparatus in a particular configuration.
Figure 14:
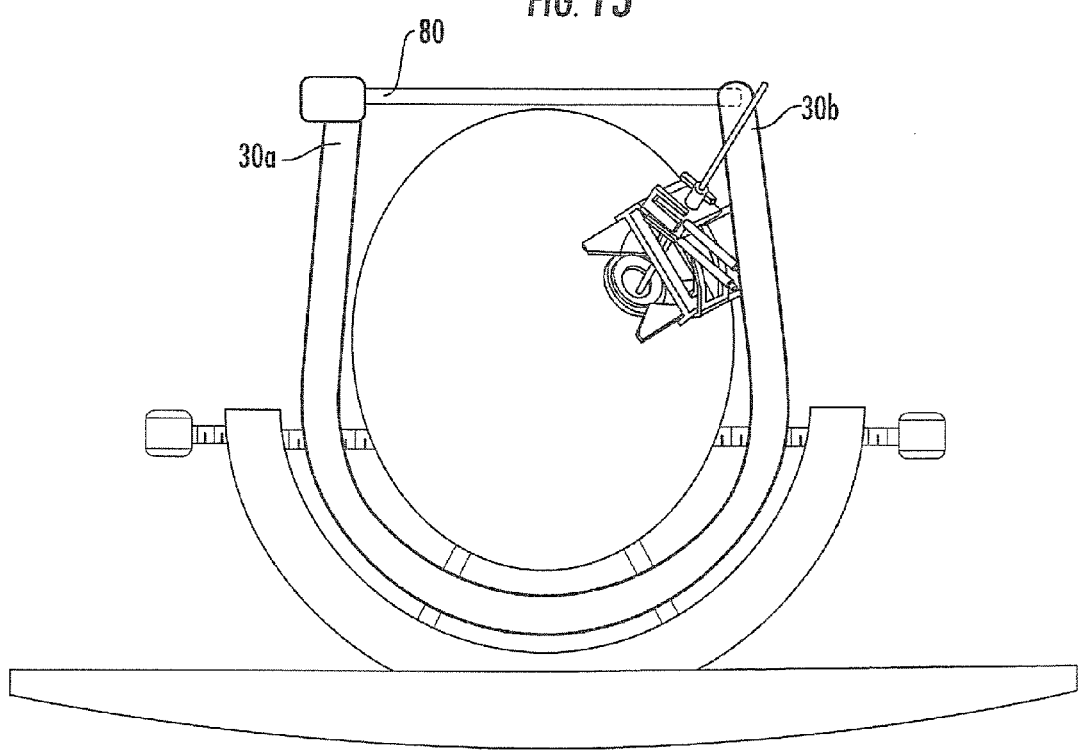
Figure 15:
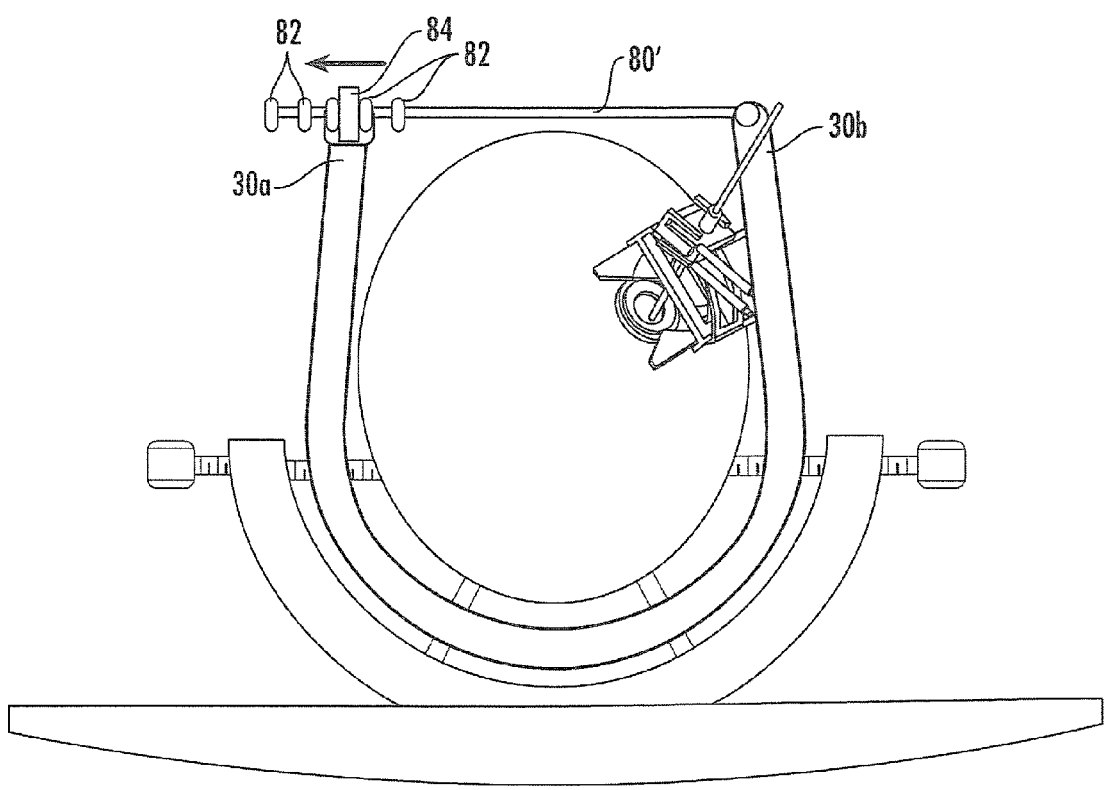

Referring now to FIGS. 13-17, a user adjustable restraining device 80 may also be attached to the respective leg portions 30a, 30b of a head coil apparatus 30 to obtain and/or maintain a user-selected spaced-apart relationship of the leg portions 30a, 30b. In some embodiments, the restraining device 80 is configured to contact a patient's head supported within the head support frame (FIG. 13). In other embodiments, the restraining device does not contact a patient's head. Various types of restraining devices may be utilized, without limitation. An exemplary restraining device is a flexible strap 80' configured to adjustably position leg portions 30a, 30b relative to each other, as illustrated in FIG. 15. The illustrated flexible strap 80' has one end secured to leg portion 30b. The opposite end of the flexible strap 80' includes a plurality of spaced apart notches 82 that are configured to engage with member 84 associated with leg portion 30a to maintain the flexible strap 80' at a length selected to maintain the leg portions 30a, 30b a desired distance from each other.

Figure 16:
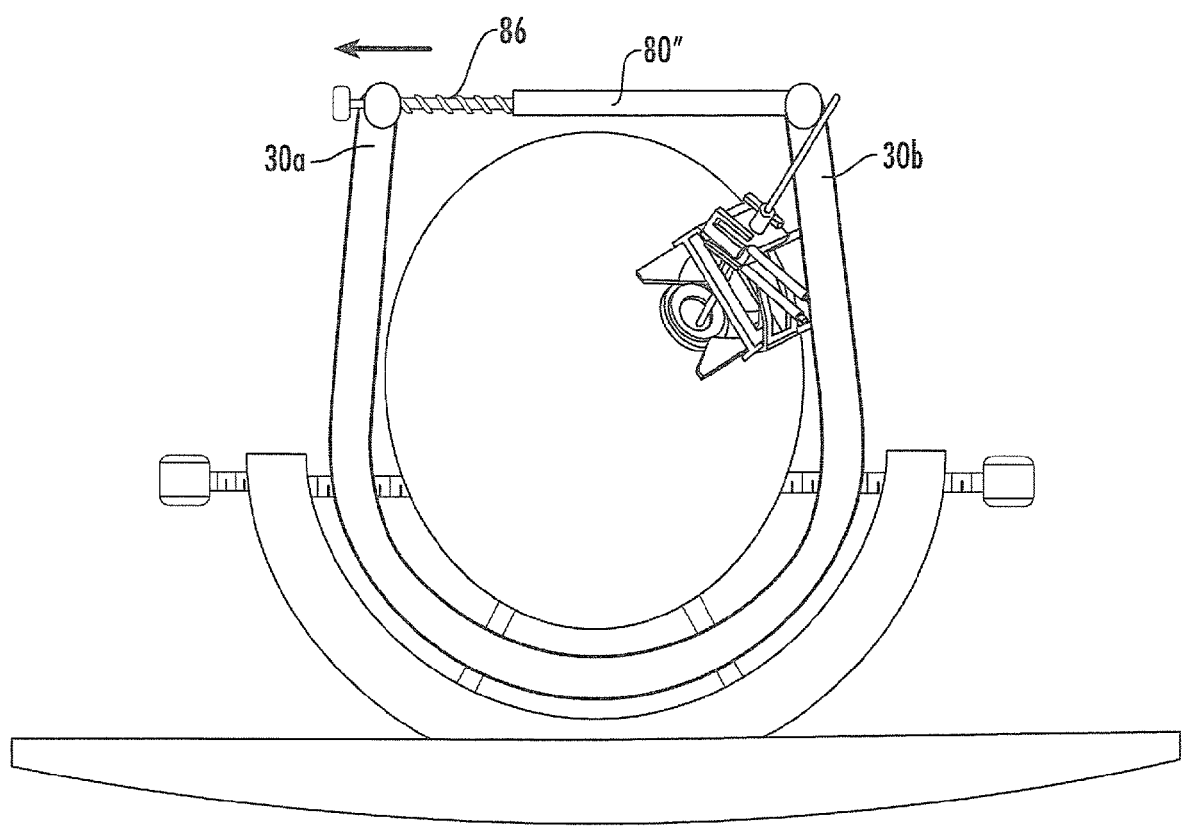

Another exemplary restraining device is a threaded member 80" configured to adjustably position leg portions 30a, 30b relative to each other, as illustrated in FIG. 16. The illustrated threaded member 80" has one end secured to leg portion 30b. The opposite end of the threaded member 80" is configured to threadingly engage a threaded rod 86 that is associated with leg portion 30a. Rotation of threaded rod 86 and threaded member 80" relative to each other is configured to move leg portions 30a, 30b relative to each other and to maintain the leg portions 30a, 30b a desired distance from each other, as would be understood by those skilled in the art.

Figure 17:
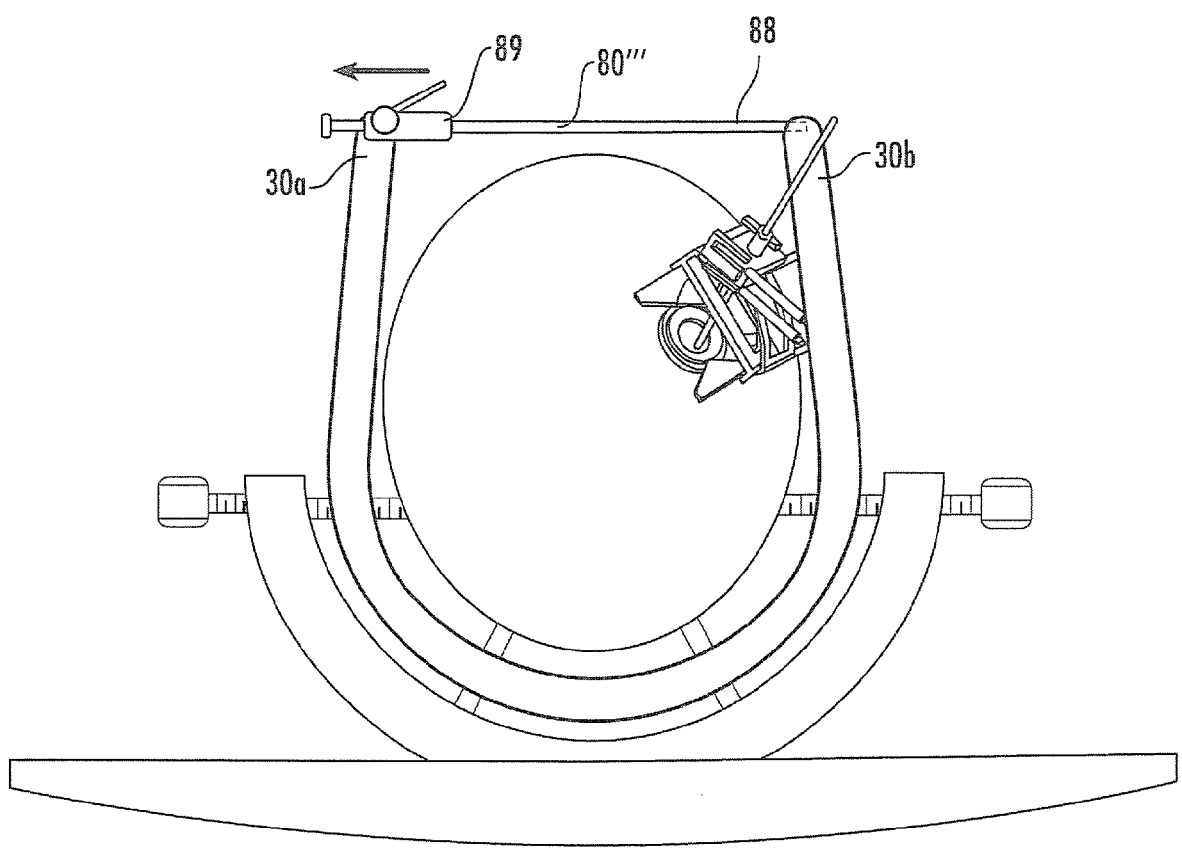

Another exemplary restraining device 80''' configured to adjustably position leg portions 30a, 30b relative to each other is illustrated in FIG. 17. The illustrated device 80''' includes an elongated member 88 having one end secured to leg portion 30b. The opposite end of the elongated member 88 is configured to be slidably received within a clamping device 89 associated with leg portion 30a. As the elongated member is pulled through the clamping device, the leg portions 30a, 30b are forced closer toward each other. Clamping device 89 is configured to maintain the leg portions 30a, 30b a desired distance from each other, as would be understood by those skilled in the art.

Figure 18:
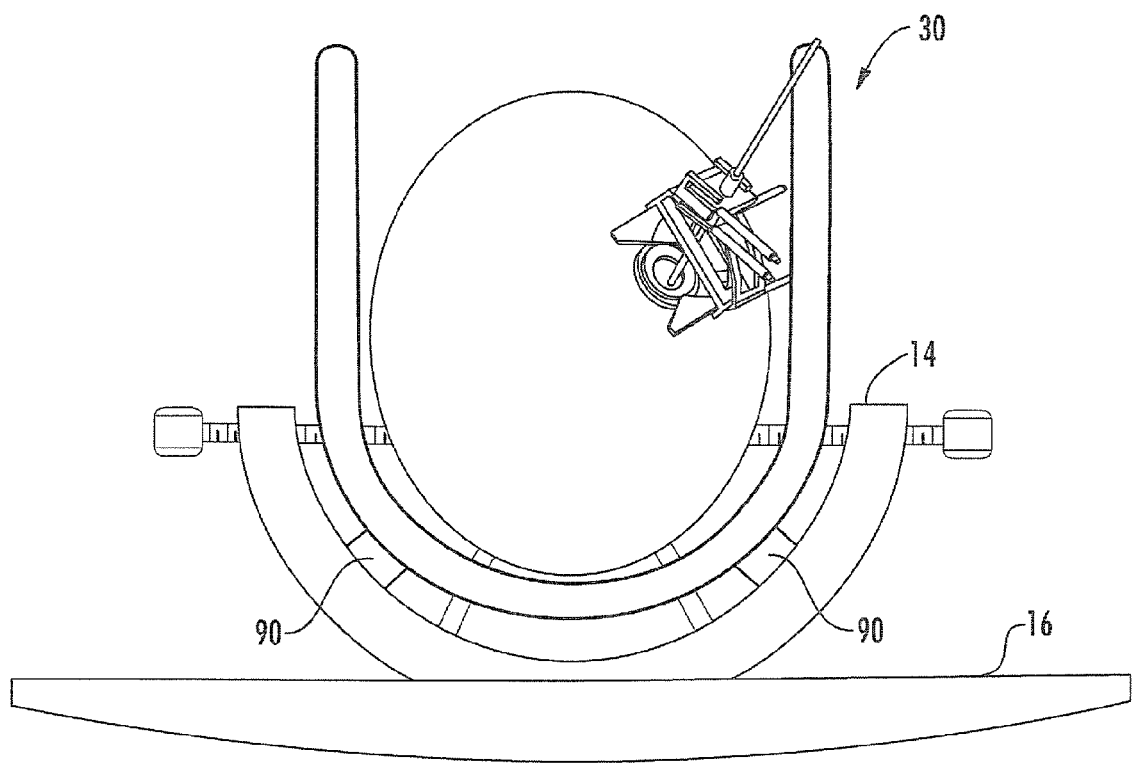
FIG. 18 is a schematic illustration of a head support assembly according to embodiments of the present invention and wherein shims are utilized to adjust the position of an open-face head coil apparatus relative to a head support frame.

Referring now to FIG. 18, an open-face head coil apparatus 30 may be adjustable in elevation relative to a head support frame 14 via spacers or shims 90 positioned between the head coil apparatus 30 and head support frame 14. These shims 90 allow a desired space to be maintained between the head support frame 14 and the head coil apparatus 30 and may allow a more customizable patient-specific fit of the open-face head coil apparatus.

Figure 19:
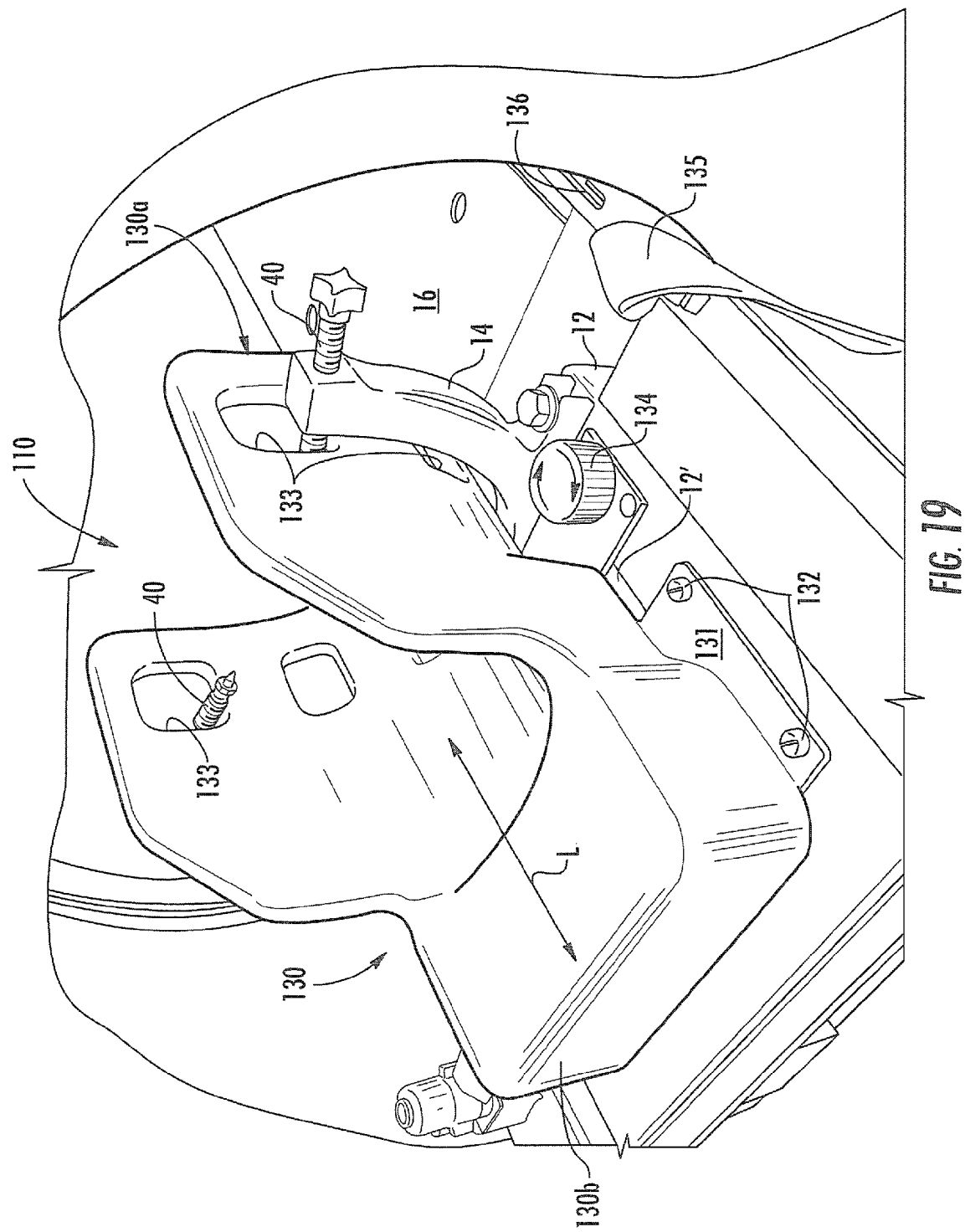
FIG. 19 is a side perspective view of a head support assembly including an alternate design of an open-face head coil apparatus, according to other embodiments of the present invention.
Figure 20:
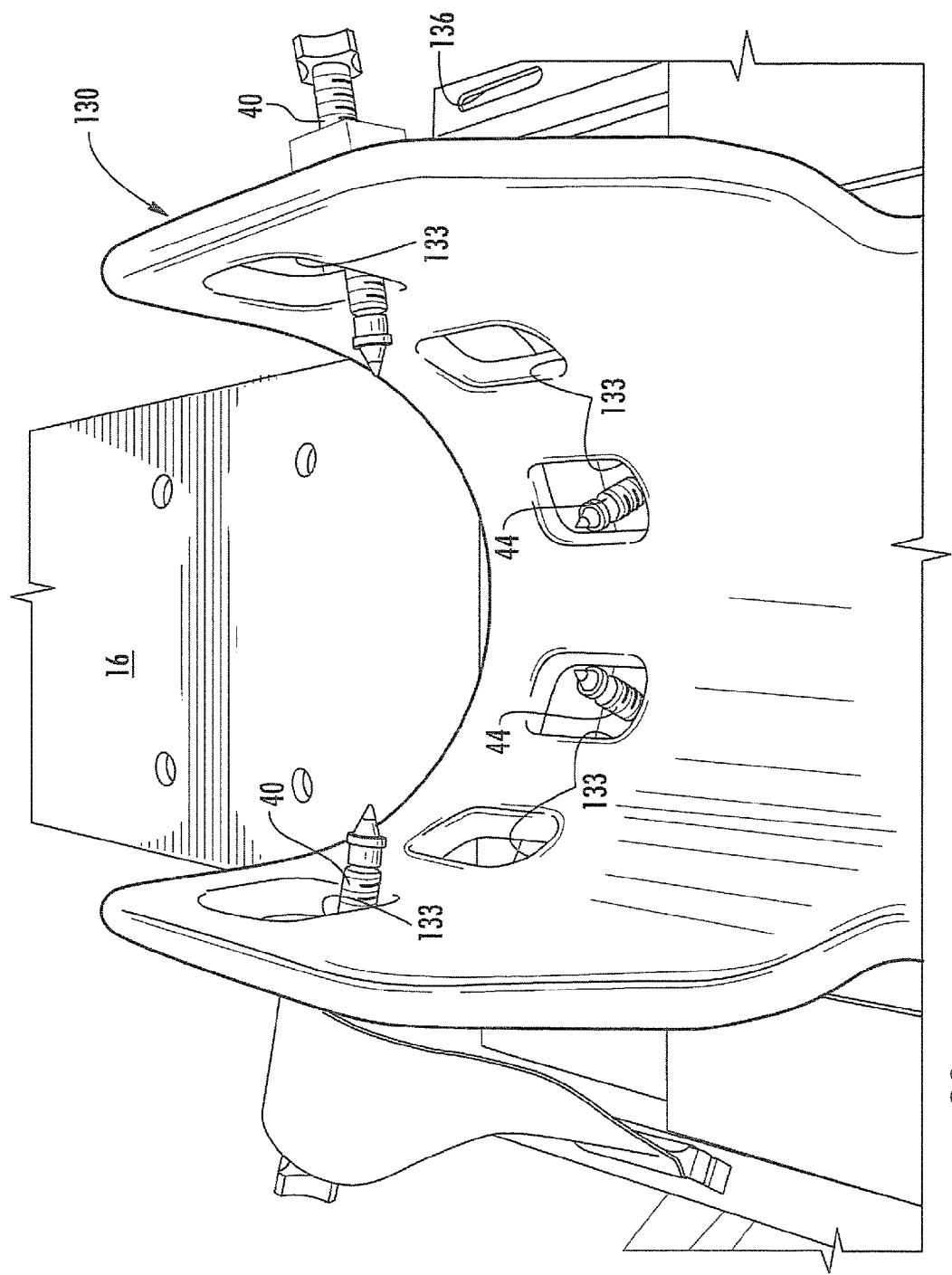
FIG. 20 is a top perspective view of the head support assembly of FIG. 19.
Figure 21A:
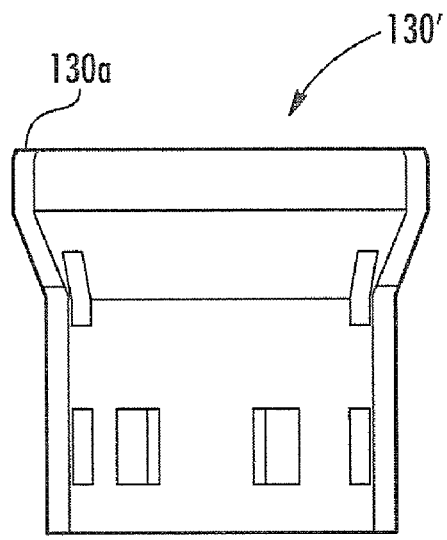
FIGS. 21A-21D are various views of an open-face head coil apparatus, according to other embodiments of the present invention.
Figure 21B:
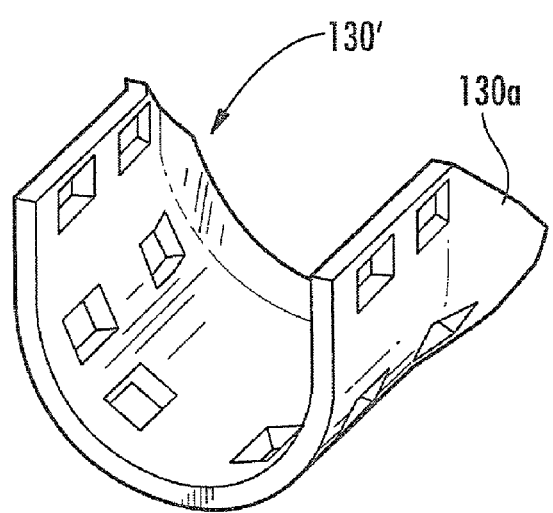
Figure 21C:
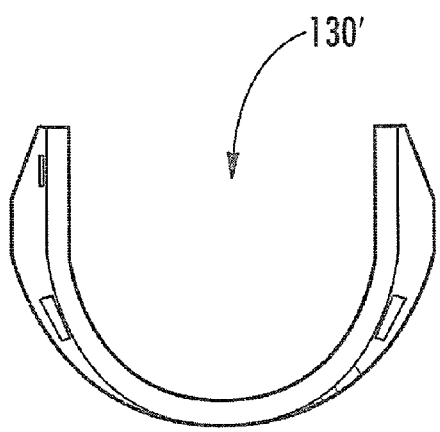
Figure 21D:
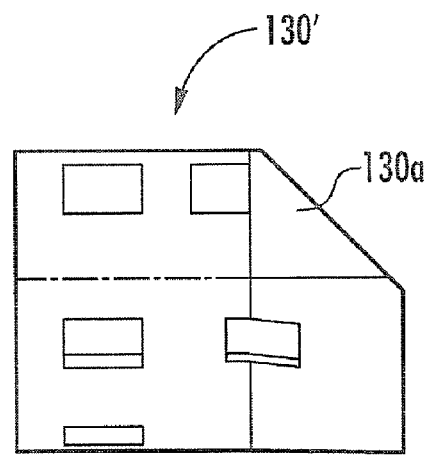
Figure 22A:
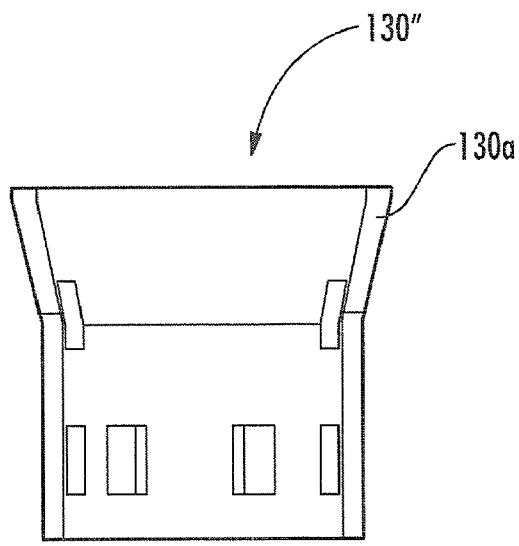
FIGS. 22A-22D are various views of an open-face head coil apparatus, according to other embodiments of the present invention.
Figure 22B:
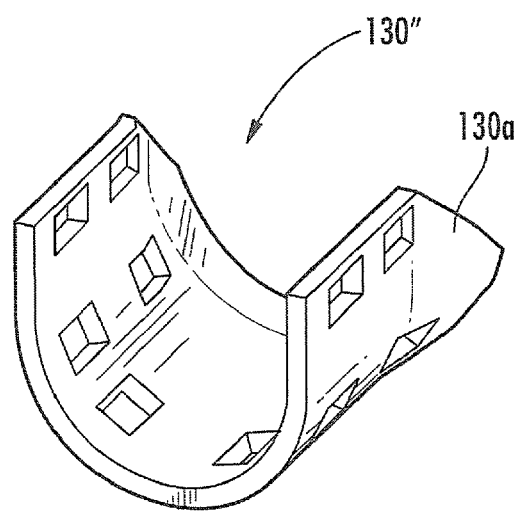
Figure 22C:
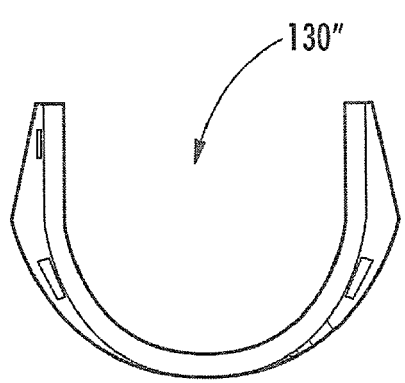
Figure 22D:
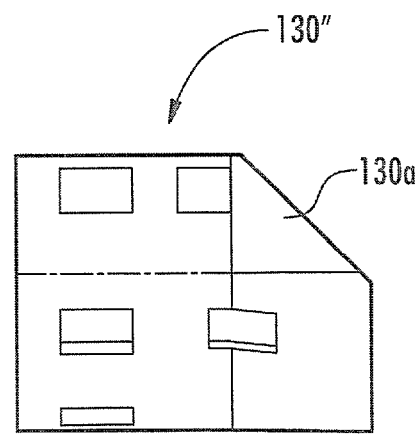

Referring now to FIGS. 19-20, a head support assembly 110 for immobilizing the head of a patient during an MRI-guided procedure, according to other embodiments of the present invention, is illustrated. The illustrated head support assembly 110 includes a base 12 that is configured to be removably secured to an MRI scanner gantry 16. A head support frame 14 is attached to the base 12. A longitudinally extending, open-face head coil apparatus 130 is also secured to the base, and is configured to surround at least a portion of a patient's head secured to the head support frame 14. The head coil apparatus 130 includes opposite first and second end portions 130a, 130b, with the first end portion 130a positioned within the head support frame 14. The head coil apparatus 130 includes a plurality of spaced-apart access windows 133 formed therein and a plurality of internal RF coils. The head coil apparatus 130 can include various numbers of RF coils, and the RF coils can be positioned in various locations. For example, there may be two (2) RF coils, three (3) RF coils, five (5) RF coils, eight (8) RF coils, etc. In some embodiments, the head coil apparatus 130 includes twelve (12) RF coils, and may be multi-channel, e.g., eight (8) channels.

The head coil apparatus 130 includes a pair of flanges (one illustrated) 131 that are used to secure the head coil apparatus to a movable portion 12' of the base 12. Threaded fasteners 132 (e.g., bolts, screws, etc.) are utilized to secure the flanges 131, and thus the head coil apparatus 130, to the base 12 as would be understood by those skilled in the art. The movable portion 12' of the base 12 is configured to move forward and backward along longitudinal direction L. Actuator 134 is configured to cause movement along the longitudinal direction L in response to rotation thereof by a user. For example, clockwise rotation of actuator 134 can cause movement of the head coil apparatus 130 along direction L (e.g., forward or backward movement), and counterclockwise rotation of actuator 134 can cause movement of the head coil apparatus 130 along direction L (e.g., forward or backward movement).

A plurality of head engagement rods 40, 44 are adjustably associated with the head support frame 14, as described above, and are configured to engage and support a patient's head within the head support frame 14. Each rod 40, 44 extends through a respective access window 133 of the head coil apparatus 130. The head coil apparatus second end portion 130b is configured to shield electronics, cables, etc. associated with the head coil apparatus 30 and extends in a direction away from the patient's head and torso.

A patient tie-down strap 135 is also illustrated in FIG. 19. This strap 135 is configured to extend over the head of a patient and over the head coil apparatus 130, and can be used to help secure the head of a patient and/or the head coil apparatus 130 and prevent movement thereof. A slot 136 in the MRI gantry 16 is also illustrated and may be utilized to receive straps for securing the head coil apparatus 130 to the MRI gantry 16, as will be described below.

FIGS. 21A-21D and 22A-22D are various views of open-face head coil apparatus 130', 130", according to other embodiments of the present invention. Each of the illustrated head coil apparatus 130', 130" is similar in structure to the head coil apparatus 130 of FIGS. 19-20, and each head coil apparatus 130', 130" is configured to be positioned within a head support frame, as described above However, head coil apparatus 130', 130" each have a respective tapered or flared end portion 130a, as illustrated. The tapered or flared end portion 130a facilitates access to a patient by a physician/clinician.

Figure 23:
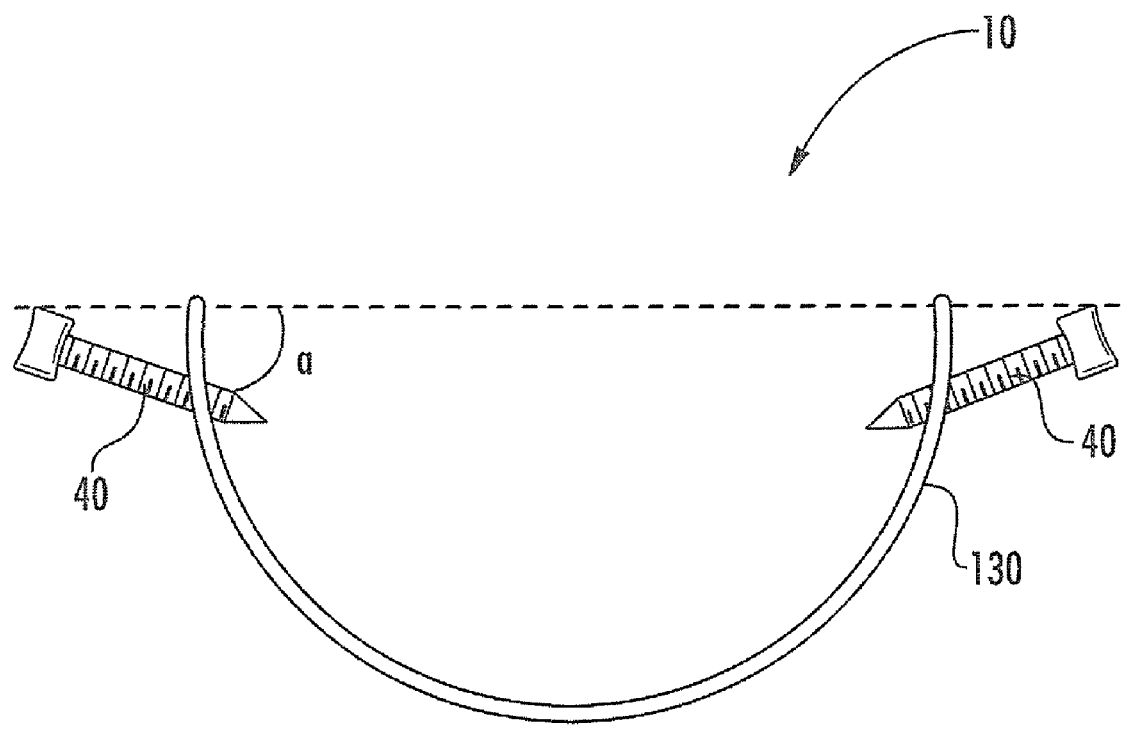
FIG. 23 is an end view of a head support assembly, according to some embodiments of the present invention, and illustrating an angled configuration of head engagement rods.

FIG. 23 is an end view of a head support assembly 10, according to some embodiments of the present invention, and illustrating that head engagement rods 40 may have an angled configuration. For example, the head engagement rods 40 may have an angle a relative to horizontal between about two degrees and thirty degrees (2°-30°), and more particularly between about five degrees and fifteen degrees (5°-15°).

Each of the illustrated head coil apparatus 30, 30', 30", 30''', 130 have an open-face and open end configuration. For example, as illustrated in FIG. 10, the head coil apparatus 30''' does not have a member extending between the two leg portions 30a, 30b or across the end portions. As such, the open-face and open end configuration of each of the illustrated head coil apparatus embodiments allows one or more targeting cannula and other interventional devices to project out of the head of a patient and into the bore of an MRI scanner magnet without being restricted. In other words head coil apparatus according to embodiments of the present invention do not interfere with interventional devices in the way that conventional head coil apparatus do.

Figure 25A:
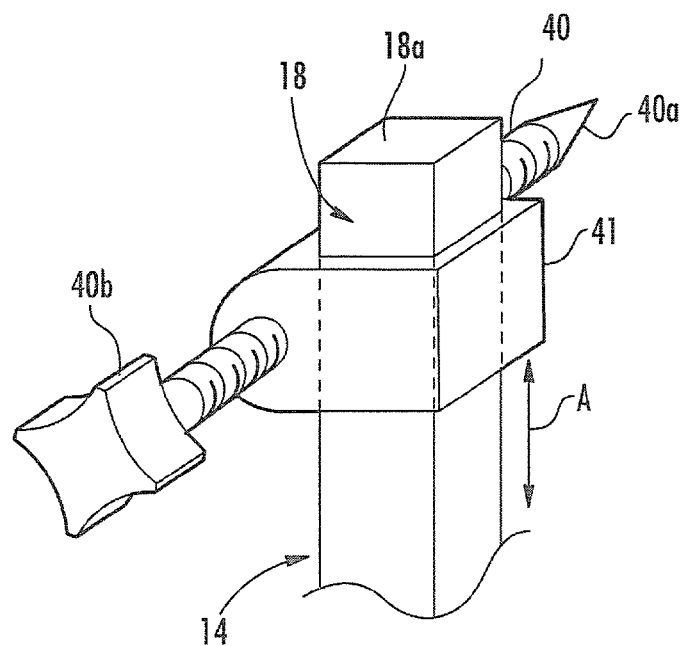
FIGS. 25A-25B are partial perspective views of head support frames, according to some embodiments of the present invention, illustrating variable position head engagement rods.
Figure 25B:
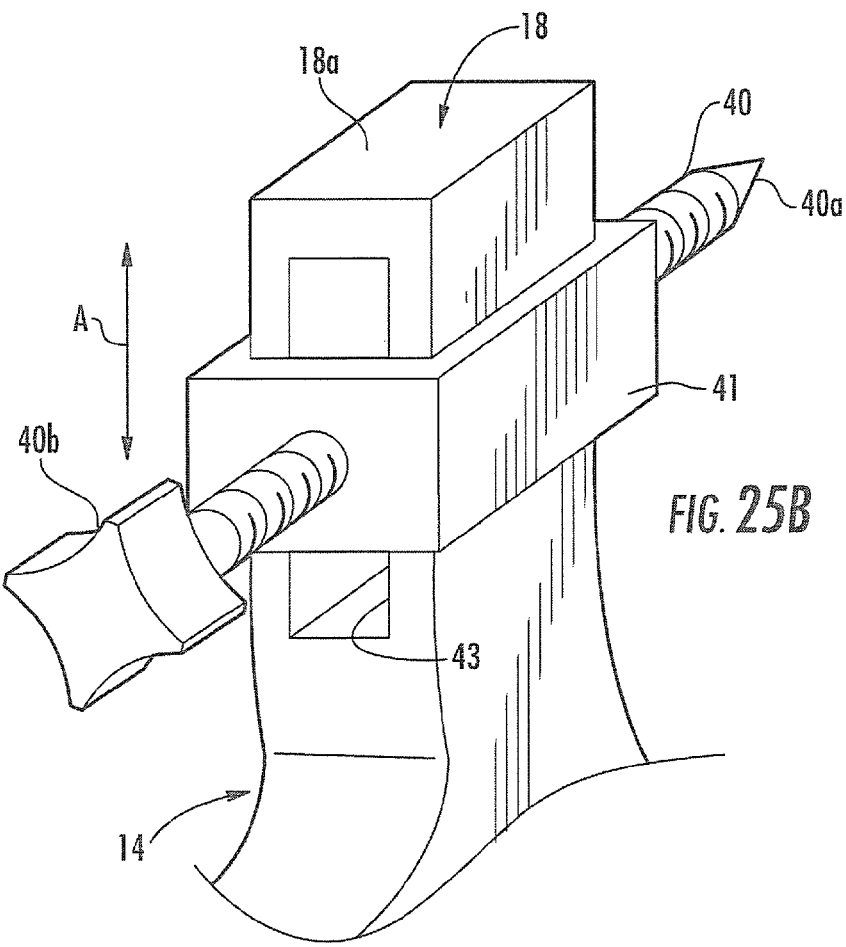

Referring to FIGS. 25A-25B, head support frames, according to some embodiments of the present invention, can have variable position head engagement rods 40. For example, in FIG. 25A, a head engagement rod 40 is movably secured to an arm 18 of a head support frame 14 via a collar 41. The illustrated collar 41 cooperates with the arm and is slidable along the arm as indicated by arrow A (e.g., up and down) relative to the arm free end 18a. Thus the head engagement rod 40 is movable proximally and distally relative to (e.g., toward and away from) the free end 18a of the arm 18. A head engagement rod 40 is threadably associated with the collar 41 and is utilized to engage the head of a patient as described above. Collar 41 can include a locking device (not illustrated), such as a set screw or bolt, for securing the collar 41 in a particular position on the arm 18. By sliding relative to the arm 18, collar 41 allows the head engagement rod to have variable positions, thereby facilitating engagement with different size heads of patients. Both head engagement rods 40 associated with a head support frame 14 can be slidable relative to a respective arm as illustrated in FIG. 25A.

In FIG. 25B, a head engagement rod 40 is movably secured to an arm 18 of a head support frame 14 via a collar 41. The illustrated collar 41 cooperates with the arm and is slidable along the arm as indicated by arrow A (e.g., up and down) relative to the arm free end 18a. Thus the head engagement rod 40 is movable proximally and distally relative to (e.g., toward and away from) the free end 18a of the arm 18. A head engagement rod 40 is threadably associated with the collar and is utilized to engage the head of a patient as described above. The arm 18 includes a slot 43 formed therethrough, as illustrated. The head engagement rod 40 extends through the slot 43 as illustrated. Collar 41 can include a locking device (not illustrated), such as a set screw or bolt, for securing the collar 41 in a particular position on the arm 18. By sliding relative to the arm 18, collar 41 allows the head engagement rod to have variable positions, thereby facilitating engagement with different size heads of patients.

Figure 26:
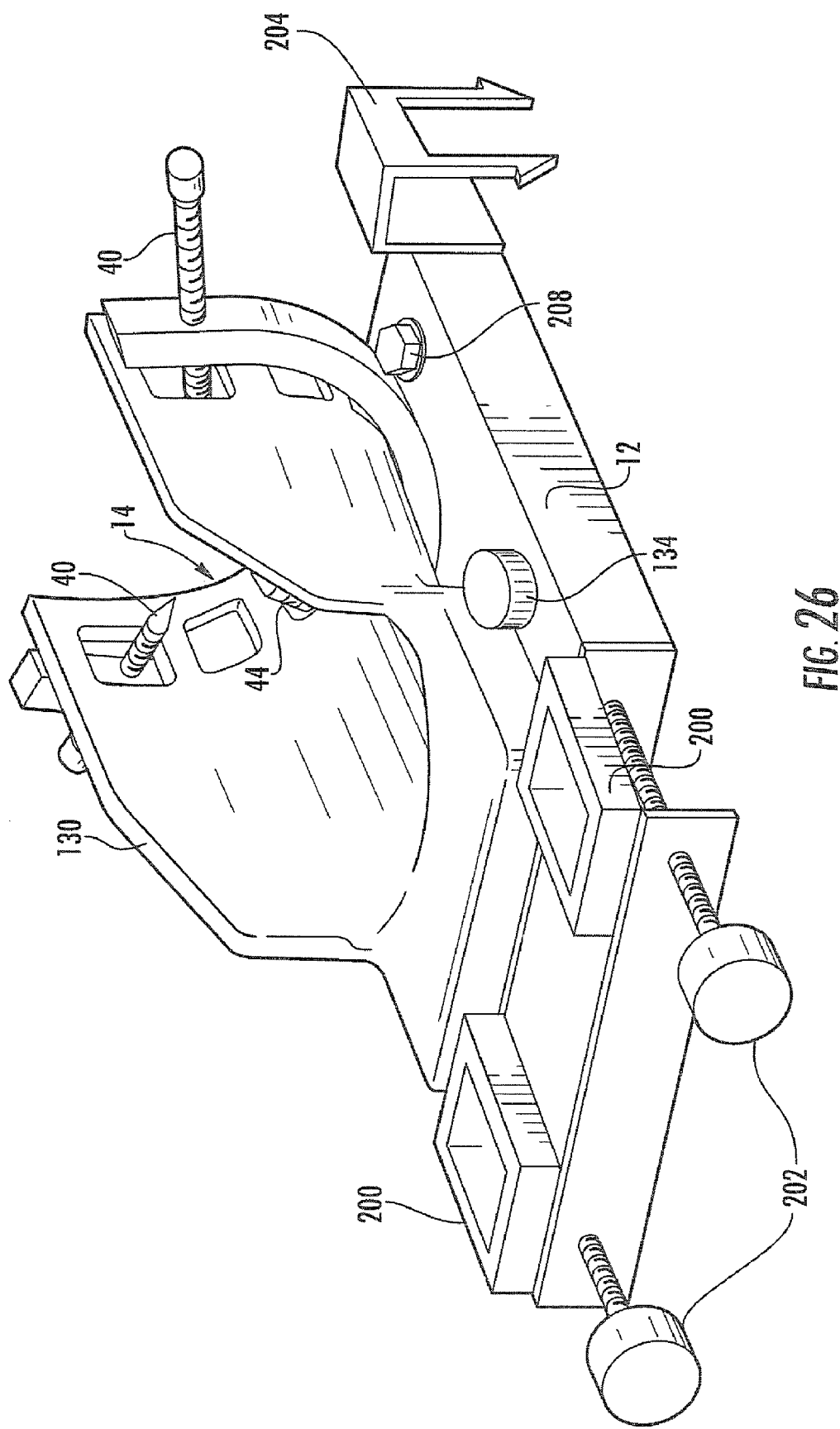
FIG. 26 is a perspective view of a base for a head support frame and head coil apparatus, according to some embodiments of the present invention.

FIG. 26 is a perspective view of a base 12 for a head support frame and head coil apparatus, according to some embodiments of the present invention. MRI scanner manufacturers use different table/gantry configurations and there are different table/gantry configurations for different models by the same MRI scanner manufacturer. The illustrated base 12 is configured to have a head support frame 14 and head coil apparatus 130 secured thereto. The base 12 is intended to be a "universal" base that is configured to be secured to different table/gantry configurations. In addition to the head support frame 14 and head coil apparatus 130, the base 12 also includes a pair of camera holders 200 for receiving MRI-compatible cameras therein. The illustrated base 12 includes a pair of clamping screws 202 in spaced-apart relationship. Clamping screws 202 are configured to lock the rear of the base 12 to an MRI scanner table/gantry. The illustrated base also includes one or more adjustable clips 204 that are configured to fasten the front of the base 12 to an MRI scanner table/gantry. For example, the clips 204 may be configured to engage slots 136 illustrated in FIG. 19. The illustrated clips 204 extend outwardly from the base 12. Adjustable straps may also be utilized in lieu of or in conjunction with the clips 204. The clips 204 may have various adjustments to facilitate securing the base to the table/gantry of different MRI scanners. The clips 204 and clamping screws 202 can individually or collectively be referred to as adjustable fasteners that facilitate securing the base 12 to different types of gantries (e.g., gantries of different MRI scanner models, different manufacturers, etc.).

The illustrated base 12 also includes an actuator 134 for adjusting the head coil apparatus relative to the head support frame 14 and/or the head of a patient. One of the bolts 208 securing the head support frame 14 to the base 12 is also illustrated.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed:

1. A head support assembly for immobilizing the head of a patient during an MRI-guided procedure, comprising:
 a base configured to be removably secured to a gantry;
 a head support frame attached to the base;
 a longitudinally extending head coil apparatus secured to the base, wherein the head coil apparatus comprises a plurality of RF coils and is configured to surround at least a portion of the patient's head within the head support frame, wherein the head coil apparatus includes opposite first and second end portions, wherein the head support frame is positioned at the first end portion of the head coil apparatus, and wherein the head coil apparatus first end portion comprises a plurality of spaced-apart access windows formed therein; and
 a plurality of head engagement rods adjustably associated with the head support frame, wherein the rods are configured to engage the patient's head within the head support frame, and wherein each rod extends through a respective access window of the head coil apparatus.

2. The head support assembly of claim 1, wherein the head coil apparatus has an open-face, substantially U-shaped configuration with spaced-apart leg portions having free ends that extend upwardly.

3. The head support assembly of claim 1, wherein the head support frame comprises a pair of arcuate members extending outwardly from the base in adjacent, spaced-apart relationship to form a substantially U-shaped head support frame.

4. The head support assembly of claim 3, wherein the arcuate arms are substantially co-planar.

5. The head support assembly of claim 1, wherein each head engagement rod extends along a respective different direction relative to a longitudinal direction defined by the head support frame.

6. The head support assembly of claim 1, wherein the longitudinally extending head coil apparatus defines a longitudinal direction and wherein the head coil second end portion extends in the longitudinal direction away from the patient's head.

7. The head support assembly of claim 1, wherein the head support frame is configured to substantially surround the head of a patient.

8. The head support assembly of claim 1, further comprising a head support frame top portion secured to the head support frame, and wherein the top portion includes at least one head engagement rod adjustably associated therewith, wherein the at least one rod is configured to engage a patient's head within the head support frame.

9. The head support assembly of claim 1, wherein the head support frame comprises a pair of elongated arms extending outwardly in adjacent, spaced-apart relationship, wherein each arm comprises a free end, and wherein at least one of the head engagement rods is movable proximally and distally relative to the free end of a respective arm.

10. The head support assembly of claim 1, wherein the base includes adjustable fasteners that facilitate securing the base to different gantries.

11. A head support assembly for immobilizing the head of a patient during an MRI-guided procedure, comprising:
 a base, wherein the base includes adjustable fasteners that facilitate removably securing the base to a gantry;
 a head support frame attached to the base;
 a longitudinally extending head coil apparatus secured to the base, wherein the head coil apparatus comprises a plurality of RF coils and is configured to surround at least a portion of the patient's head within the head support frame, wherein the head coil apparatus includes opposite first and second end portions, wherein the head support frame is positioned at the first end portion of the head coil apparatus, and wherein the head coil apparatus first end portion comprises a plurality of spaced-apart access windows formed therein;
 a plurality of head engagement rods adjustably associated with the head support frame, wherein the rods are configured to engage the patient's head within the head support frame, and wherein each rod extends through a respective access window of the head coil apparatus; and
 at least one camera holder attached to the base, wherein the camera holder is configured to receive an MRI-compatible camera therewithin.

* * * * *